(12) United States Patent
Barnes

(10) Patent No.: US 8,462,354 B2
(45) Date of Patent: Jun. 11, 2013

(54) AIRCRAFT ICING DETECTOR

(75) Inventor: William J. Barnes, Miami, FL (US)

(73) Assignee: Lumen International Inc., Miami, FL (US)

( * ) Notice: Subject to any disclaimer, the term of this patent is extended or adjusted under 35 U.S.C. 154(b) by 450 days.

(21) Appl. No.: 12/902,494

(22) Filed: Oct. 12, 2010

(65) Prior Publication Data

US 2012/0085868 A1    Apr. 12, 2012

(51) Int. Cl.
*G01B 11/24* (2006.01)
*G01N 21/55* (2006.01)

(52) U.S. Cl.
CPC ............... *G01B 11/24* (2013.01); *G01N 21/55* (2013.01)
USPC .......................................... 356/601; 356/445

(58) Field of Classification Search
CPC ................................. G01B 11/24; G01N 21/55
USPC ................... 356/601–624, 445–448
See application file for complete search history.

(56) References Cited

U.S. PATENT DOCUMENTS

| | | | |
|---|---|---|---|
| 5,301,905 A * | 4/1994 | Blaha | 244/134 F |
| 5,760,711 A * | 6/1998 | Burns | 340/962 |
| 6,052,056 A * | 4/2000 | Burns et al. | 340/583 |

OTHER PUBLICATIONS

Dr. Daniel Bower, "Circuit City Cessna 560," NTSB, Pueblo, CO, Feb. 16, 2005.
FAA "FAA Requires Ice Protection Changes for Transport Aircraft," Aug. 4, 2009.

* cited by examiner

*Primary Examiner* — Michael P Stafira
(74) *Attorney, Agent, or Firm* — Michael J. Buchenhorner

(57) ABSTRACT

A method for aircraft surface contamination detection and measurement includes: mounting a laser probe on an airfoil; positioning the laser probe to emit laser energy at multiple pre-determined surface points along the leading edge of the airfoil; and using a processor device for activating the laser probe and obtaining measurement data for generating a surface contour of the shape and accurate measurement of the depth of airfoil icing in the surface target area. The icing data is presented to the pilot in a display that alerts him to the icing and accurately shows the depth and shape of the airfoil icing.

29 Claims, 32 Drawing Sheets

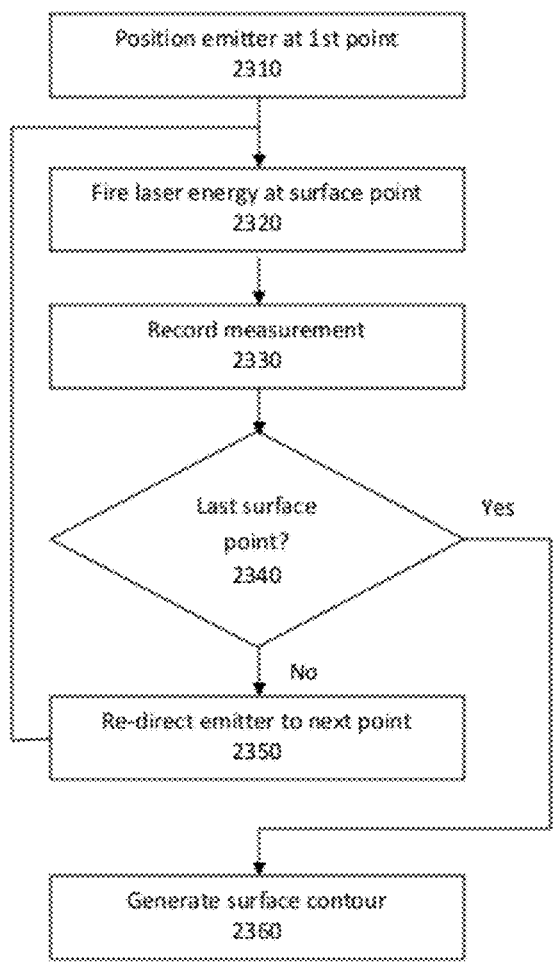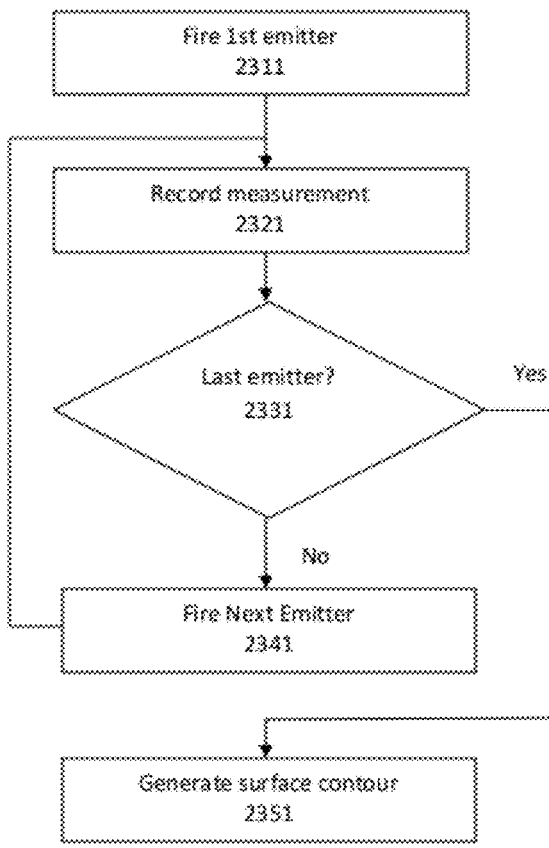
*FIG. 23a*
*FIG. 23b*

AIRCRAFT ICING DETECTOR

CROSS-REFERENCE TO RELATED APPLICATIONS

None.

STATEMENT REGARDING FEDERALLY SPONSORED-RESEARCH OR DEVELOPMENT

None.

INCORPORATION BY REFERENCE OF MATERIAL SUBMITTED ON A COMPACT DISC

None.

FIELD OF THE INVENTION

The invention disclosed broadly relates to the field of ice detection systems for airplanes and more particularly relates to the field of laser-enabled ice detection systems.

BACKGROUND OF THE INVENTION

Recent air travel incidents involving ice on aircraft wings have underscored the necessity of detecting the presence, depth, and shape of ice on aircraft wings while in flight. It is difficult to see ice or frost (usually clear or whitish) against a light-colored airplane wing from the cockpit, and even if ice is detected visually in flight, it is almost impossible to accurately determine the thickness of the ice and the rate of accumulation.

The main parts of an airplane are the: cockpit, fuselage, wings, powerplant (engines), landing gear, and the empennage. The wings are attached to each side of the fuselage and these are the main lifting surfaces of the airplane. The wing tip is at the end of the airplane furthest from the fuselage. Ailerons are attached to the rear, or trailing, edges of the wings. Wings have a leading edge at the front. The empennage, or tail section, can include a vertical stabilizer (fin), rudder, a horizontal stabilizer and elevator.

The basic problem is that there is no simple, cost-effective system that will warn a pilot when he first encounters icing in flight and once in icing conditions, there is no system to provide feedback to the pilot on the effectiveness of his anti-icing procedures.

Current systems do not provide the depth and shape of the ice accretion on the aircraft. There is no real-time display of the type of icing. Important factors for a pilot to know are: What shape? How much? and Is the ice increasing or decreasing? This is important because ice shape and depth greatly affects aircraft performance and stall speed. For example, ice horns can provide extreme disruption to the airflow over a wing and are often the final icing shape that leads to a stall. Ice horns are ice formations that are formed perpendicular to relative wind. They are created when outward pressure carves ice into two "horns" that disrupt the airflow and decrease the effectiveness of the wing, greatly increasing stall speed.

Different airfoil shapes collect ice differently in common icing scenarios. The aerodynamic response varies with the shape of the ice on an airfoil (wing). Iced wings can stall without warning at a higher speed than clean wings. The amount of aerodynamic degradation depends on: 1) type of ice; 2) amount of ice accumulation; 3) droplet size; 4) airspeed; 5) flap settings; 6) angle of attack; and 7) asymmetric wing loading. A "clean" wing stalls from back to front giving plenty of airframe buffet warning to the pilot, while an "iced" wing stalls from front to back with little or no warning.

Currently, icing is difficult or impossible to detect at night. Large commercial aircraft have wing illumination lights, but the wings are commonly too far behind the cockpit for easy viewing, or the visible portion of the wing is so far away from the cockpit that subtle changes in ice formations are not observable. The presence of ice on the wings is often detected by observing ice on another part of the aircraft, such as a windshield wiper bolt, rather than by visual observation of the wing itself. Visual inspection is unreliable under conditions of limited visibility brought on by fog, falling snow, freezing rain, and/or by darkness.

Therefore, there is a need for a method to detect the presence and accumulation of aircraft surface contaminants such as ice or frost.

SUMMARY OF THE INVENTION

Briefly, according to an embodiment of the invention a method for aircraft surface contamination detection and measurement includes steps or acts of: mounting a laser probe at the leading edge of an airfoil; positioning the laser probe to emit laser energy aimed at a plurality of pre-determined surface points along a leading edge of the airfoil, wherein a receiver array includes a surface target area from which to receive the reflected laser energy to measure the difference between the normal reflected laser location and the observed reflected laser location due to the presence of ice or other contaminants on the leading edge of the wing. The emitted laser beams are directed to a plurality of calibrated receiving sensors mounted on a second surface on the aircraft or on a receiver probe.

The method further includes steps of: generating a first referential measurement of a surface contour of the surface target area; analyzing a reflected energy difference to sense a surface contour of the surface target area by generating measurement data by: iteratively generating a differential measurement of the surface contour; iteratively calculating a difference between the first referential measurement and the differential measurement as a difference measurement; storing the measurement data; determining that a surface contamination event has been detected if the difference measurement exceeds a pre-determined amount; and transmitting event information about the event.

The measurement data for generating the surface contour is used to determine the amount, the shape, the severity, and the type of the event. Further, a timing device is used for accumulating a temporal history of the surface contamination event and this temporal history is stored and used to indicate a trend of the event.

According to another embodiment of the present invention, a system for aircraft icing detection and measurement includes: a first laser probe mounted on a first surface of the airfoil (such as the wing); a plurality of calibrated receiving sensors for receiving the reflected laser energy; a processor device; storage; an input/output interface; and a memory operatively coupled with the processor. The system can further include a pilot display and storage for storing measurement data and a temporal history of icing events. The calibrated receiving sensors are mounted on a second surface of the aircraft, such as the fuselage or a stall fence.

According to another embodiment of the present invention, the receiving sensors are disposed on a second laser probe mounted on the first surface. The receiving sensors can be arranged within a sensor array.

According to another embodiment of the present invention, a display for presenting icing event information includes: an operable coupling with a processor device; a screen for presenting icing event information; an operable coupling with a timing device; a plurality of indicators; and a sub-display of a timing event and a current outside ambient temperature reading.

The method can also be implemented as machine executable instructions executed by a programmable information processing system or as hard coded logic in a specialized computing apparatus such as an application-specific integrated circuit (ASIC).

BRIEF DESCRIPTION OF THE SEVERAL VIEWS OF THE DRAWINGS

To describe the foregoing and other exemplary purposes, aspects, and advantages, we use the following detailed description of an exemplary embodiment of the invention with reference to the drawings, in which:

FIG. 23a is a flowchart of the single emitter method, according to an embodiment of the present invention;

FIG. 23b is a flowchart of the multiple emitter method, according to an embodiment of the present invention;

Figure 1:
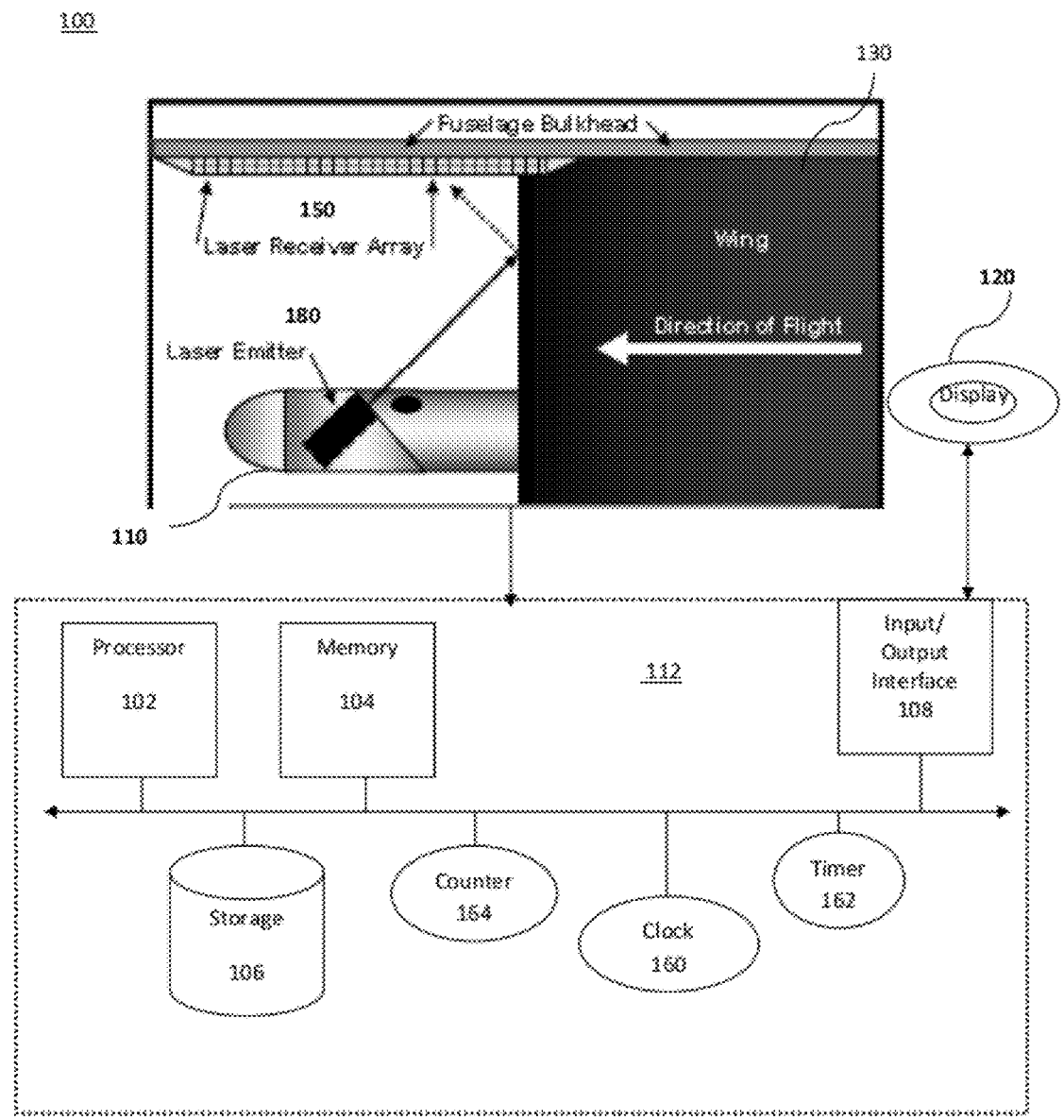
FIG. 1 shows a simplified illustration of the laser detection system, according to an embodiment of the invention.
Figure 2:
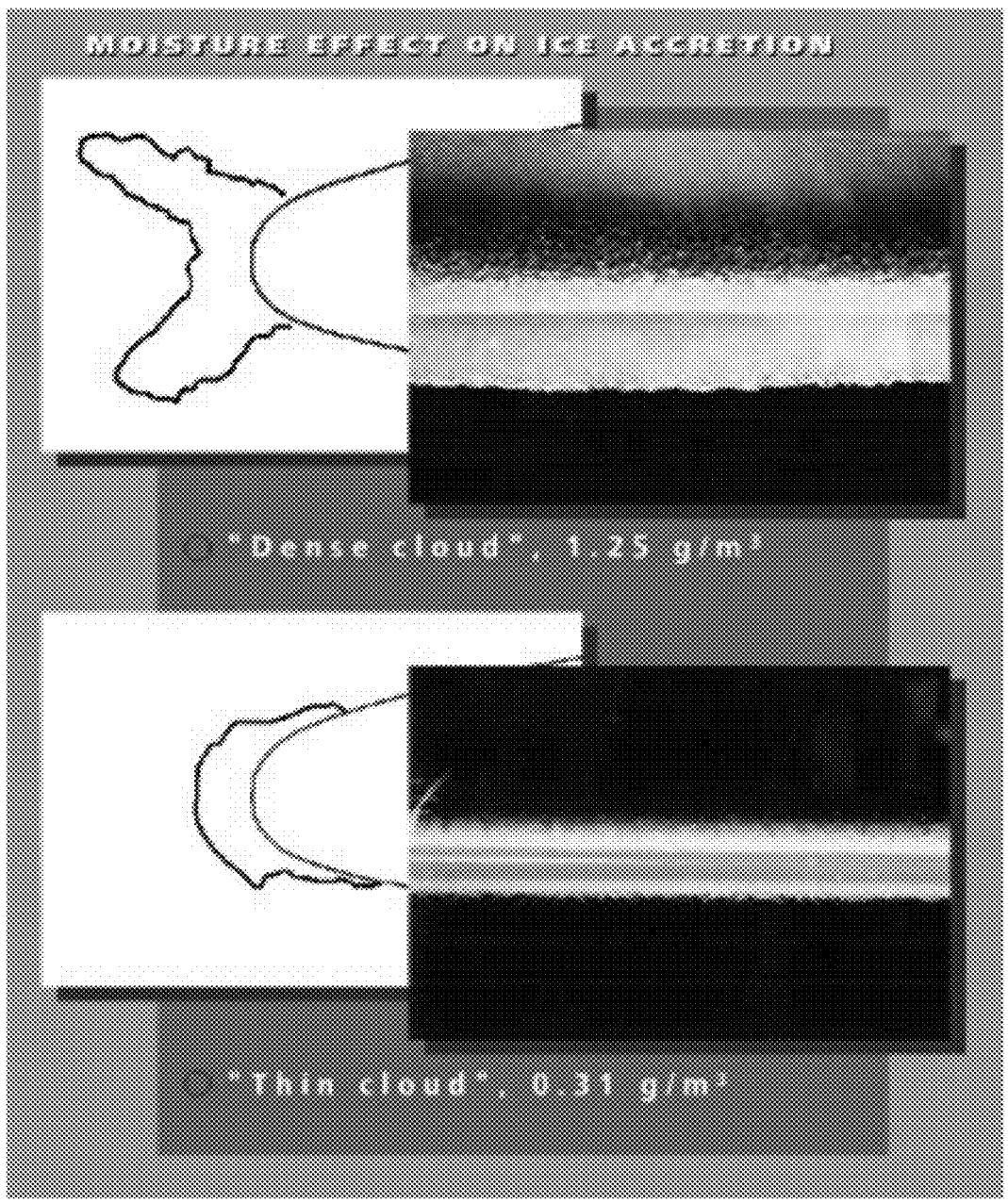
FIG. 2 is an illustration showing the moisture effect on ice accretion of two different ice shapes, according to the known art.
Figure 3A:
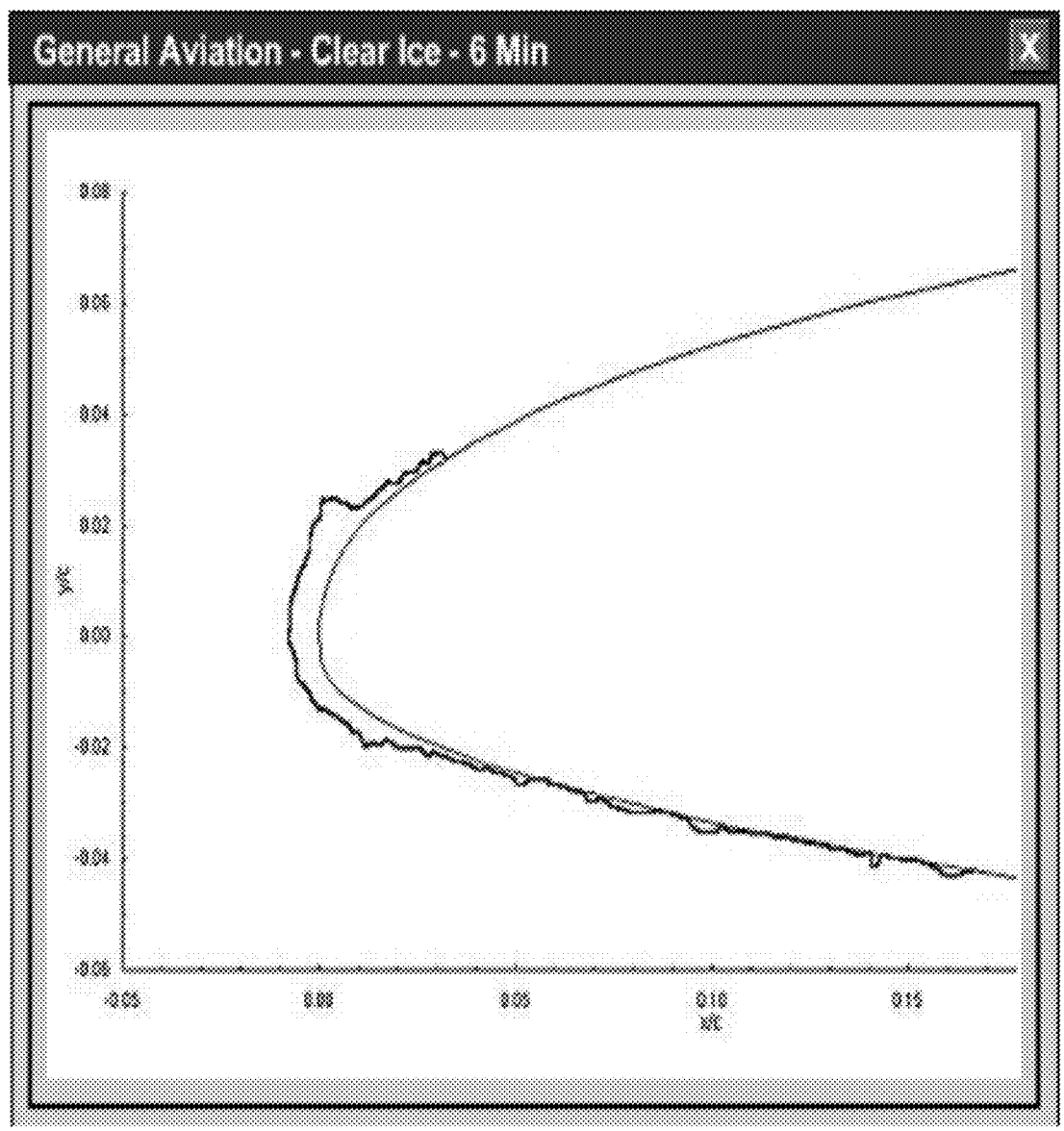
FIGS. 3a, 3b, and 3c shows the aerodynamic responses to three different airfoil shapes, according to the known art.
Figure 3B:
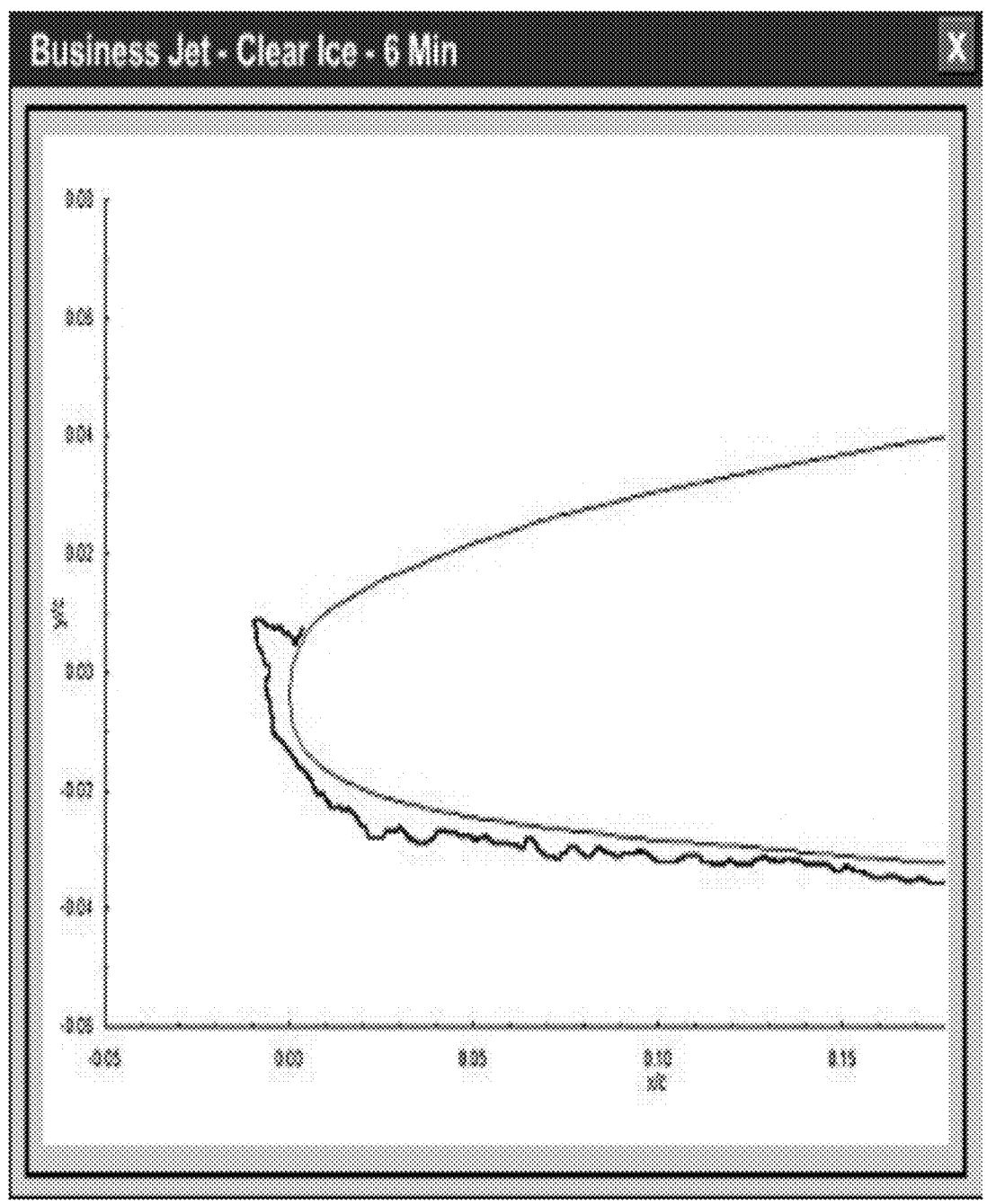
Figure 3C:
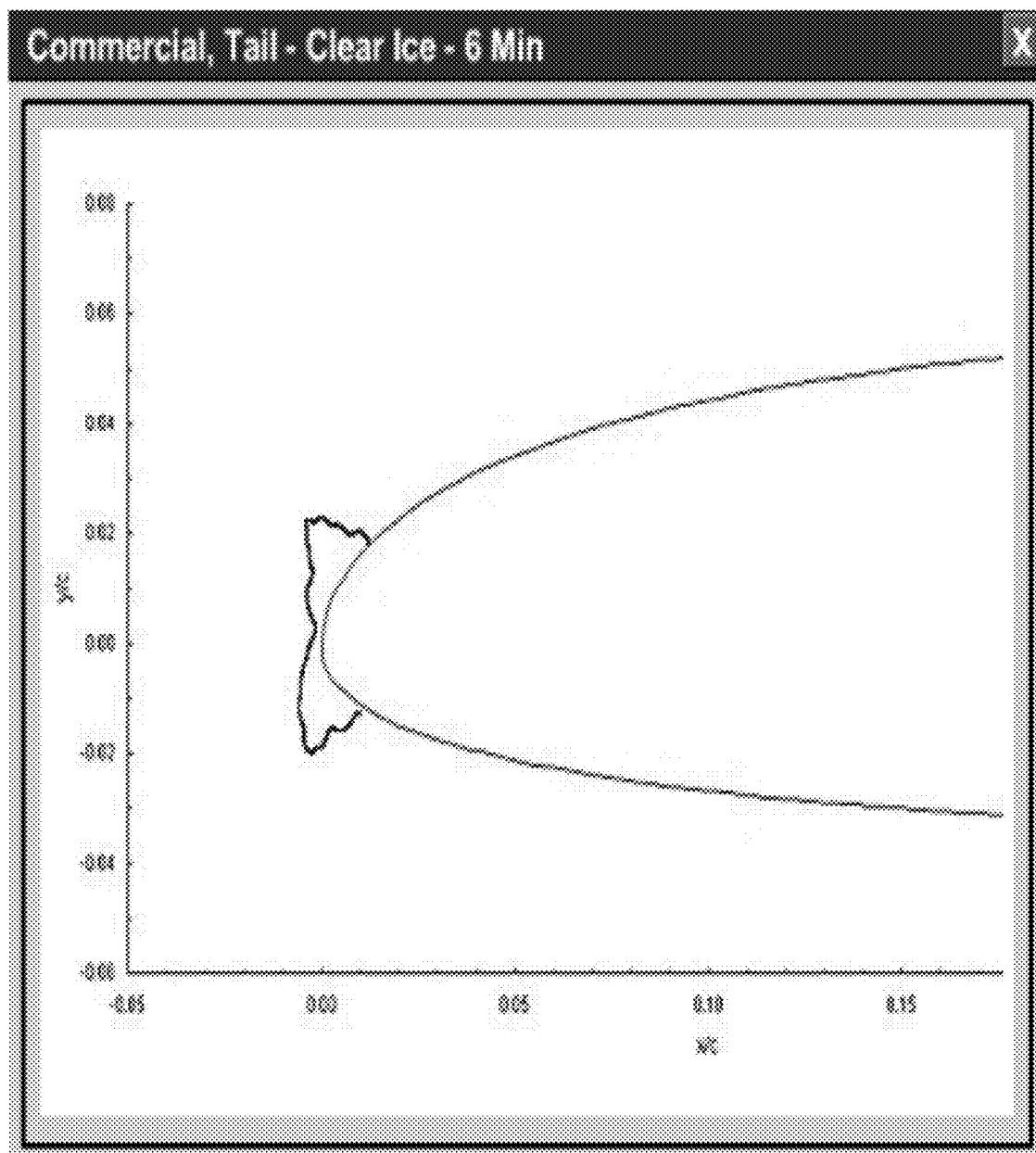
Figure 4A:
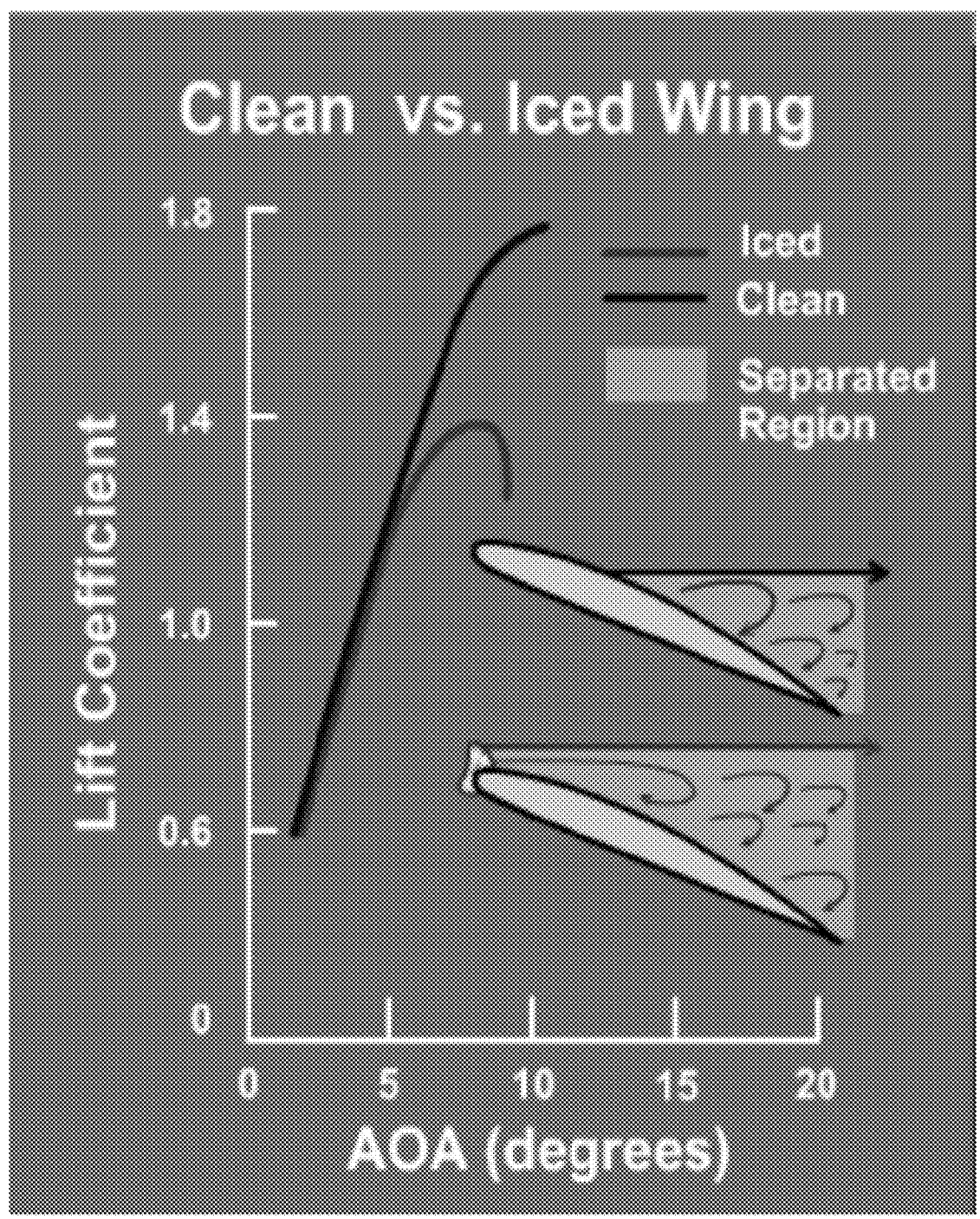
FIG. 4a shows a graph illustrating the amount of aerodynamic degradation of a clean wing vs. an iced wing, according to the known art.
Figure 4B:
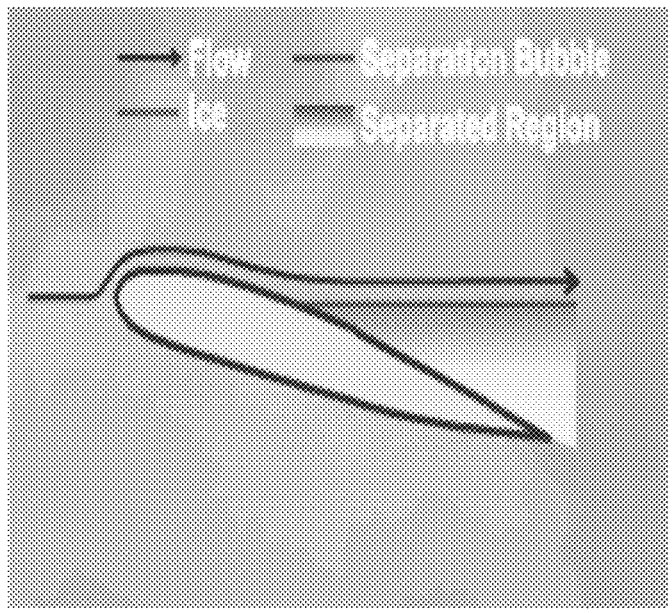
FIGS. 4b and 4c are simplified illustrations of a clean wing at stall, according to the known art.
Figure 4C:
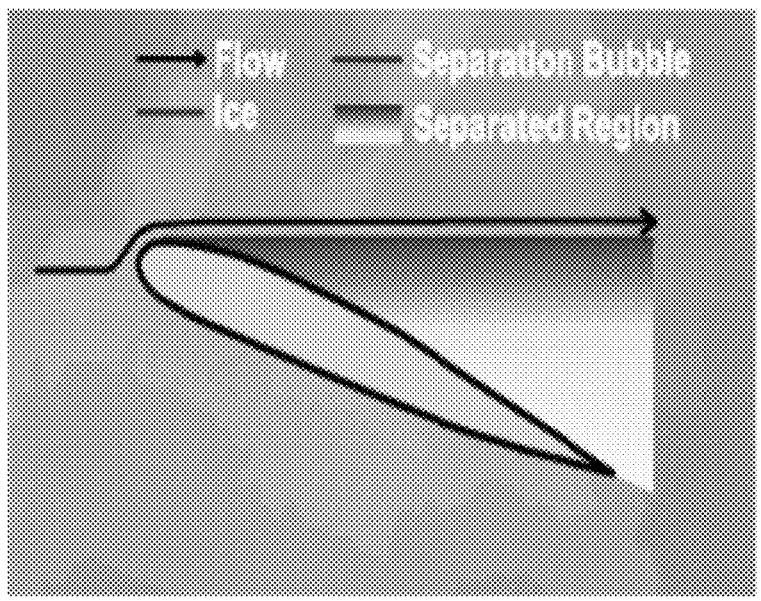
Figure 5A:
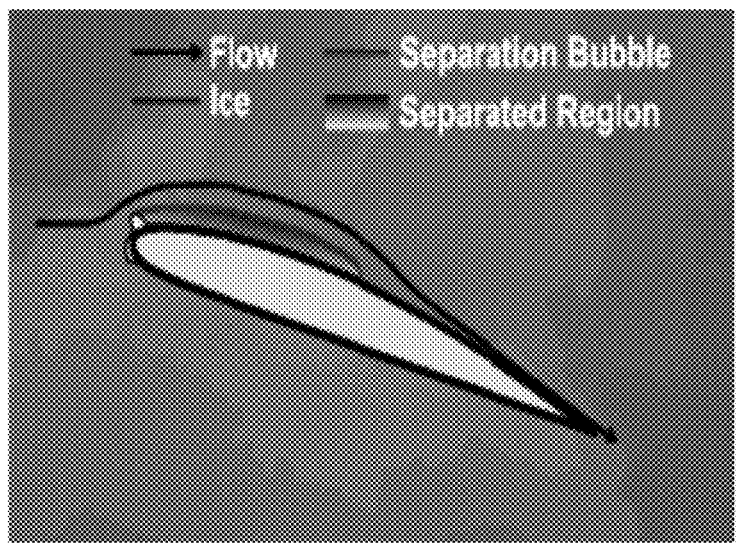
FIGS. 5a and 5b are simplified illustrations of an iced wing at stall, according to the known art.
Figure 5B:
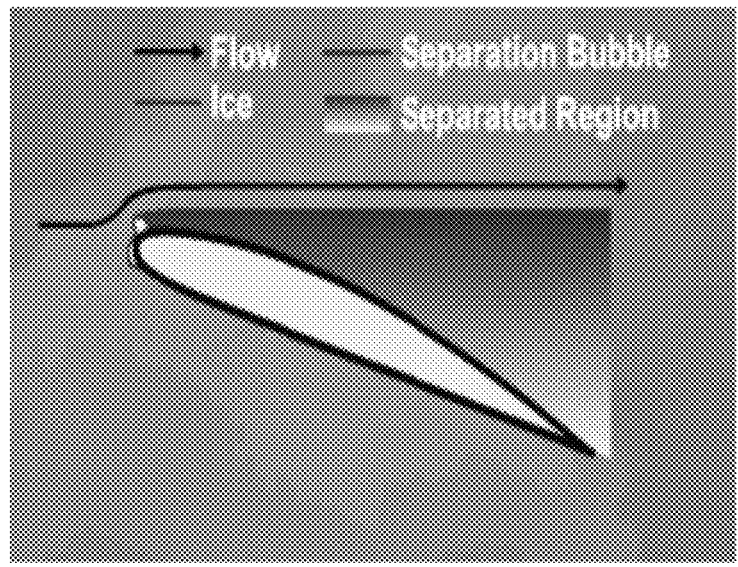

While the invention as claimed can be modified into alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the scope of the present invention to detect aircraft icing in flight by laser measurements.

DETAILED DESCRIPTION

We describe a system, apparatus, and method for providing a laser-enabled "airframe contamination" alert to provide information on the amount and shape of an accumulation of surface contaminants such as ice or frost, on an airfoil as well as details of the surface contamination event. The system, apparatus, and method are suitable for use in general aviation (private), military, corporate, and commercial aircraft. Embodiments of the invention can also be advantageously employed with unmanned aerial vehicles (UAV).

An embodiment of the system combines a laser-based surface contaminant detection device with a pilot display to warn pilots of the initial formation of airframe contaminants. The notification and details of the surface contamination event can also be down-linked to the Federal Aviation Administration (FAA) or other agencies via various existing radio frequency (RF) links.

In the following description, numerous specific details are set forth by way of exemplary embodiments in order to provide a more thorough description of the present invention. It will be apparent, however, to one skilled in the art, that the present invention may be practiced without these specific details. In other instances, well-known features have not been described in detail so as not to obscure the invention. The preferred embodiments of the inventions are described herein in the Detailed Description, Figures and Claims. Unless specifically noted, it is intended that the words and phrases in the specification and claims be given the ordinary and accustomed meaning as understood by those of skill in the applicable art. If any other meaning is intended, the specification will specifically state that a special meaning is being applied to a word or phrase.

The terminology used herein is for the purpose of describing particular embodiments only and is not intended to be limiting of the invention. As used herein, the singular forms "a," "an," and "the" are intended to include the plural forms as well, unless the context clearly indicates otherwise. The term "airfoil" in its broadest definition refers to "a device that provides reactive force when in motion relative to the surrounding air; can lift or control a plane in flight" or "the shape of a wing or blade." Thus the term airfoil can encompass the wings and the tail of an airplane and even the blades of a helicopter or windmill. Although embodiments of the present invention can be advantageously implemented on all those objects falling within the broadest definition of airfoil (wings, rudder, stabilizers, helicopter blades, turbine blades, windmill blades), for purposes of clarity, we will limit our description of the embodiments to a more narrow definition of an airfoil, to wit: "The Airfoil is the shape of the cross section of the wing. The front of the airfoil is the leading edge and is usually a rounded section. The back of the airfoil is the trailing edge and usually tapers to nearly a point. The distance between the two is the wing chord. The top surface of the airfoil is usually always curved to allow smooth airflow and produce lift." (from http://www.flyingsites.co.uk/newcomers/intros/aircraftterms.htm).

Also for simplicity we limit our descriptions and examples to airplanes; however those with knowledge in the art will understand that other forms of aircraft can be contemplated within the spirit and scope of the invention. Additionally, although the invention can be advantageously employed for detecting various surface contaminants such as ice or frost, we will describe the apparatus and system with respect to ice detection.

The Ice Detection System.

The ice detection system 100 according to an embodiment of the present invention includes the laser probe device 110 with at least one laser emitter 180, laser detection sensors 150 located in a second probe (not shown) or at other locations on the aircraft, the pilot display 120, and a computational sub-system 112.

The computational sub-system 112 is represented here as a high-level block diagram. The computational sub-system 112 includes inter alia a processor device 102 which communicates with sensors 150, input devices, and output devices via an input/output interface 108. Input devices may include, for example, a keyboard, a mouse, a scanner, an imaging system or the like. Output devices may include, in addition to the pilot display 120 shown here, printers, or other devices. The pilot display 120 may be a touch-screen display.

The sub-system 112 further includes a memory 104, and storage 106 all computationally connected through a bus architecture or other means. The input/output interface 108 is operatively coupled with the pilot display 120. The processing sub-system 112 can further include a counter 164, a clock 160, and a timer 162, among other components.

The pilot display 120 can be a CDTI (cockpit display of traffic information of the FAA) display that is tied into the Federal Aviation Administration (FAA) to provide aeronautical weather and operational data to cockpit displays with fully integrated weather and navigation functions. For use with an unmanned aircraft, the pilot display 120 will be presented off-site, such as on a manned aircraft, to the ground terminal, or other location.

The clock 160 (for example an accurate crystal oscillator) provides a time history to correspond with icing events reported by the laser probe 110. The clock 160 can be configured to provide a time signal to correspond with signals emitted by the sensors 150. The processor 102 records the time signal together with the sensor signal in order to provide a temporal history that can be mapped to a status history. The history data can be stored in the memory 104 and/or storage 106, along with other information about the icing events (such as depth, location, type of ice, and shape of ice formation).

Tying events to a time stamp provides for a more meaningful history of events because it can indicate a trend in icing conditions (whether the ice is worsening of improving). The timer 162 records a length of time for an icing event, then resets to zero after no ice is detected. The temporal history is preferably presented graphically, as a graph or chart.

In addition to receiving uplinked data from an agency such as the FAA, the aircraft can also provide data to the agency. The location and altitude of the aircraft is known by the agency; therefore by receiving information regarding the icing event, the agency ground systems can generate a three-dimensional pictorial representation of the area and altitudes of icing and send it out to other aircraft so that they can avoid the icing conditions. This is similar to today's systems where the FAA receives weather radar information from the National Weather Service and blends it into the displays of air traffic controllers and uplinks the data to aircraft for display on their CDTI screens. In this invention, the cockpit display 120 can receive information from different approved government and commercial sources plus in situ and remote sensors.

The ice detection system 100 is operable to provide continuous icing event information to a pilot or other observer during a flight. Additionally, the system 100 can store and transmit temporal histories of icing or other contamination events that occurred during a flight. In an embodiment of the present invention, the data recorded for a flight can be either immediately transmitted to the FAA or other agency, or temporarily stored onboard and downloaded after the end of the flight. This data can prove to be invaluable to the FAA or other agencies in maintaining a safe flight pattern for other aircraft, as well as for use in accident or incident reconstruction.

The Laser Probe.

Figure 6:
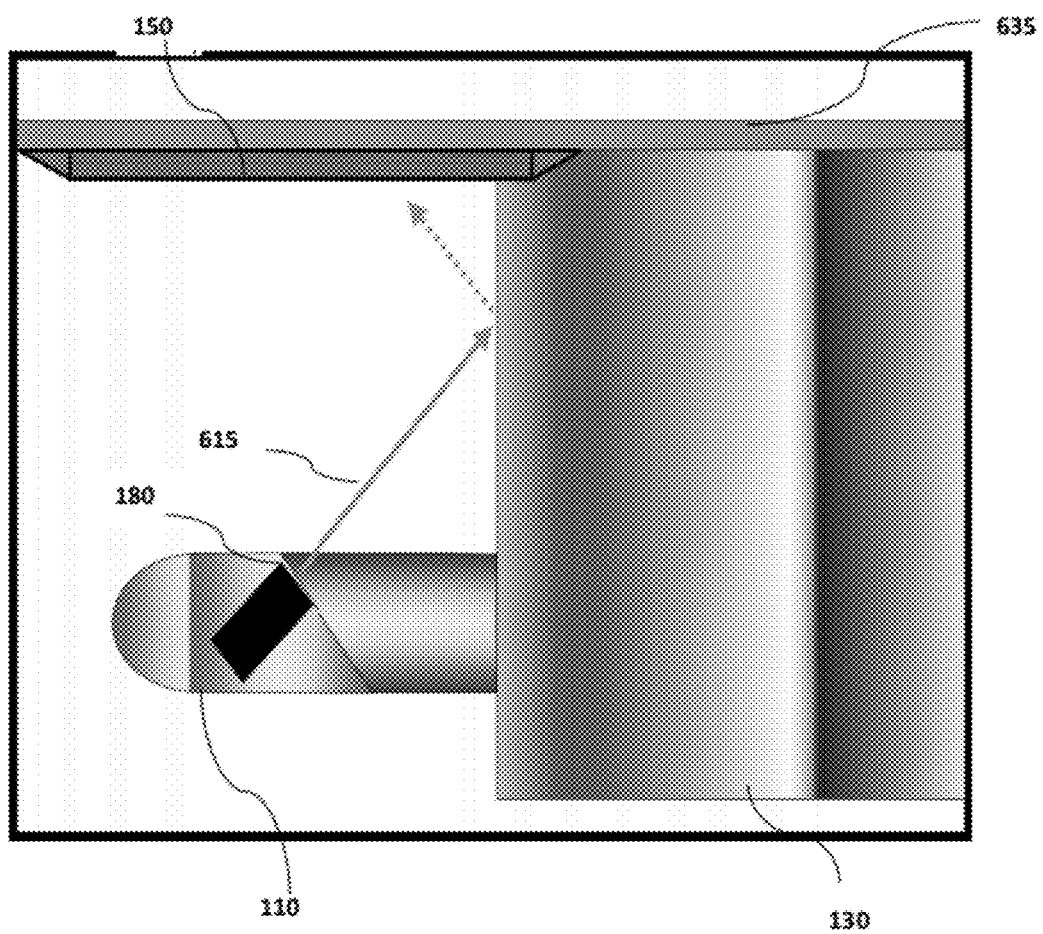
FIG. 6 shows a top view of a mounted laser probe with laser emitters according to an embodiment of the present invention.

The probe 110 is a laser device that contains at least one laser emitter 180 used to verify the known geometry from the probe 110 to specific points on an airfoil surface 130, such as an airplane wing or horizontal stabilizer. Any type of laser may be used, but a blue-green (532 nanometer) laser is preferred because of its ability to penetrate water. See FIG. 6 showing a top view of the probe 110 mounted in front of the airfoil 130 to direct laser energy 615 at a specific point on the leading edge of the airfoil 130 from each individual laser emitter. Note that in the case of multiple laser emitters, they are fired separately and a measurement is calculated for each firing. It is the aggregation and plotting of these individual measurements that produces the surface contour. The laser may be presented in the form of a dot, spot, line or other predetermined pattern. FIG. 6 also shows a part of the fuselage or stall fence 635 on the aircraft.

Figure 7:
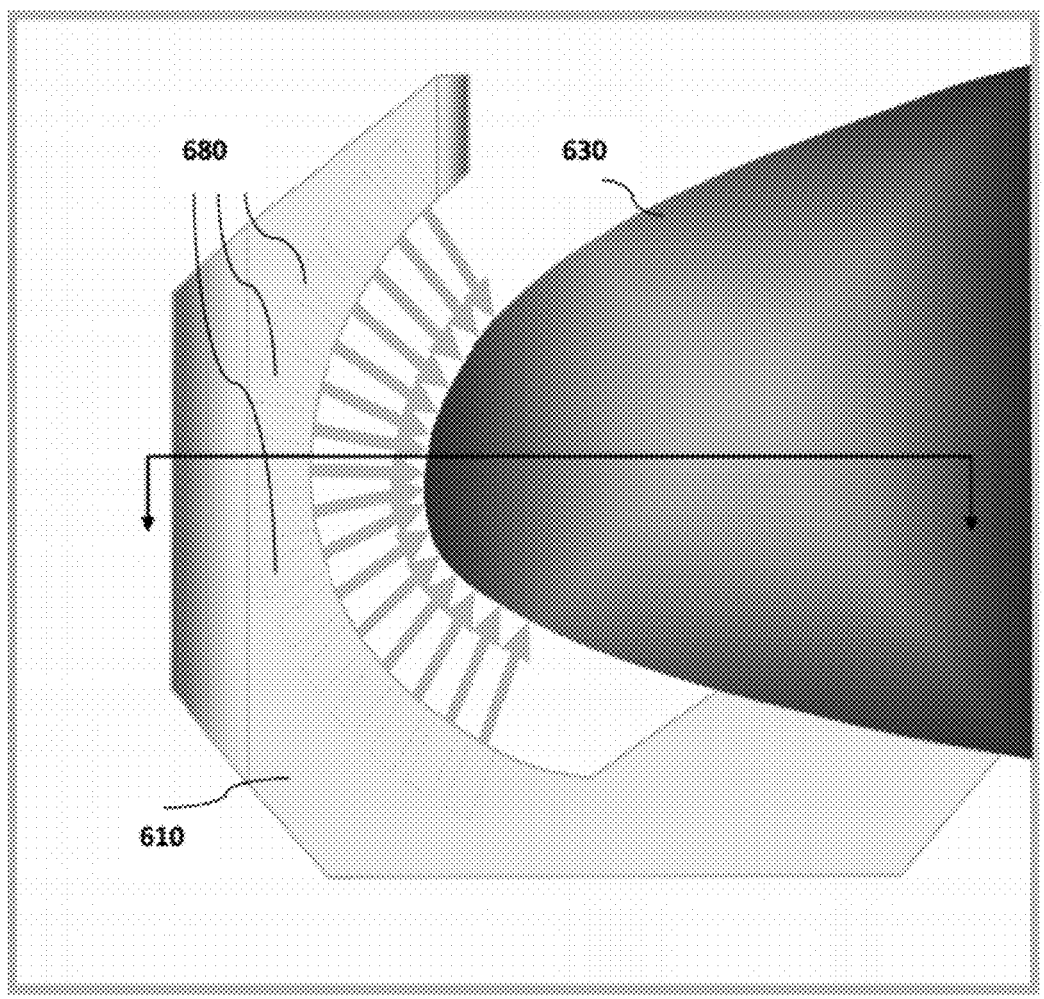
FIG. 7 shows an illustration of a cross-section of the mounted laser probe through the wing, according to an embodiment of the present invention.

FIG. 7 shows a cross-section view of the laser probe 610 through the wing 630. The laser emitters 680 are shown in this illustration. The system 100 can include one laser probe 110 mounted on the wing or horizontal stabilizer. Or the system 100 can include dual probes 110 mounted on each wing; or dual probes mounted on both sides of the horizontal stabilizer, or both. Any configuration of one to four probes is possible.

The probe 110 may be heated or unheated, but would typically be heated to avoid having accumulated ice interfere with the laser pattern. The laser probe 110 uses a laser light source 615 to illuminate a portion of the wing that is reflected along a predicted path into a calibrated receiving sensor to detect the abnormal reflection/refraction of the laser source that occurs when small ice crystals first form on the surface. The correlated measurements from each firing of a laser emitter are mathematically combined to derive the actual shape of the surface contour of the wing leading edge as affected by the ice accumulation.

Single Emitter Embodiments.

Figure 8A:
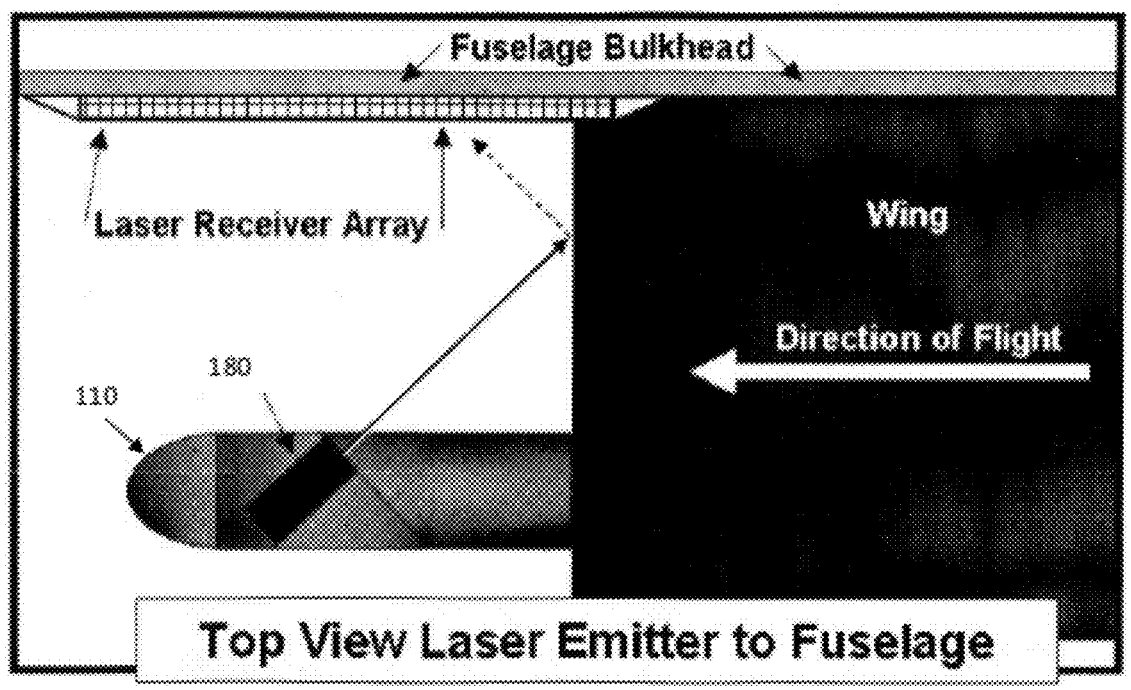
FIG. 8a shows a top view of a laser emitter to fuselage, according to an embodiment of the present invention.

In one embodiment of the present invention shown in FIG. 8a, a single emitter laser probe 110 is mounted on the wing and/or horizontal stabilizer. This embodiment is preferable for lower tier aircraft. The laser probe 110 is preferably constructed of a dense, stiff material such that the probe remains steady even when the wing exhibits movement in flight. The probe 110 is secured from the bottom of the airfoil surface, extending out beyond the wing leading edge. The laser probe 110 can be attached to the bottom surface by conventional means such as bolting it to the wing. The attachment must be a robust attachment so that the probe 110 is not loosened in flight.

Figure 24:
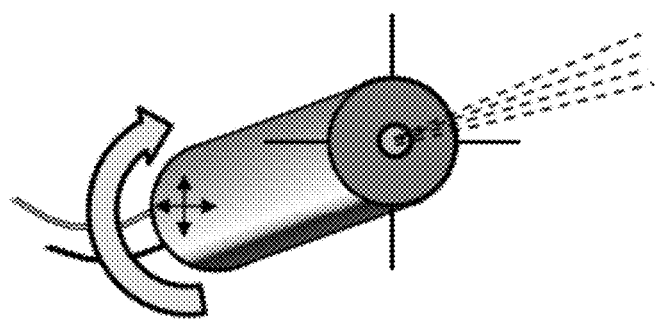
FIG. 24 is an illustration of a single rotating laser emitter with a rotating cam, according to an embodiment of the present invention.
Figure 25:
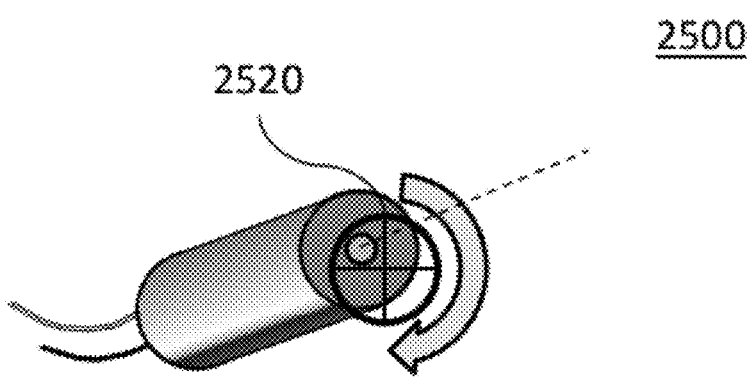
FIG. 25 is an illustration of a single fixed laser emitter with a rotating lens, according to an embodiment of the present invention.

In a single emitter embodiment, one emitter is used to fire laser energy at designated surface points. The single laser 110 will fire a vertical laser line intermittently at the wing. The ice will deform the shape of the reflected line. Note that the surface points are selected to be close to the probe 110, but not directly in front of the probe. The single emitter is calibrated to target pre-determined surface points along the leading edge of the airfoil. The laser probe in one single emitter embodiment need not move; rather the laser emitter is redirected by either optical or mechanical means as illustrated in FIGS. 24 and 25.

Referring now to FIG. 23a, the emitter is positioned to direct laser energy at the first designated surface point at step 2310. Next, in step 2320 the processor device 102 activates the probe 110 to fire laser energy at the first surface point. With each firing of laser energy, measurements are taken in step 2330.

If the emitter is positioned at the last in the series of surface points as determined at decision step 2340, then the surface contour is generated at step 2360. Else at step 2350, the emitter is re-positioned to fire at the next pre-determined surface point, until measurement data from all surface points is collected.

Rotating Laser Emitter Embodiment.

Referring now to FIG. 24 there is shown an illustration of a laser emitter 2400 that is redirected via mechanical means. The rotating laser emitter 2400 has a body fixed on a rotating off-center cam to vary the location of the emitted laser beam by moving the aft end of the emitter 2400.

Fixed Laser Emitter Embodiment.

Referring now to FIG. 25 there is shown an illustration of a fixed laser emitter 2500 that uses optical movement to redirect the laser energy. Fixed laser emitter 2500 has a lens 2520 that rotates to vary the location of the emitted laser beam. The exemplary lens 2520 depicted here has four segments to enable slight changes to the direction of the beam. The lens 2520 may be configured with many other variations in the number and size/shape of the lens segments, as can be appreciated by those with knowledge in the art.

Multi-Emitter Embodiment.

Figure 9:
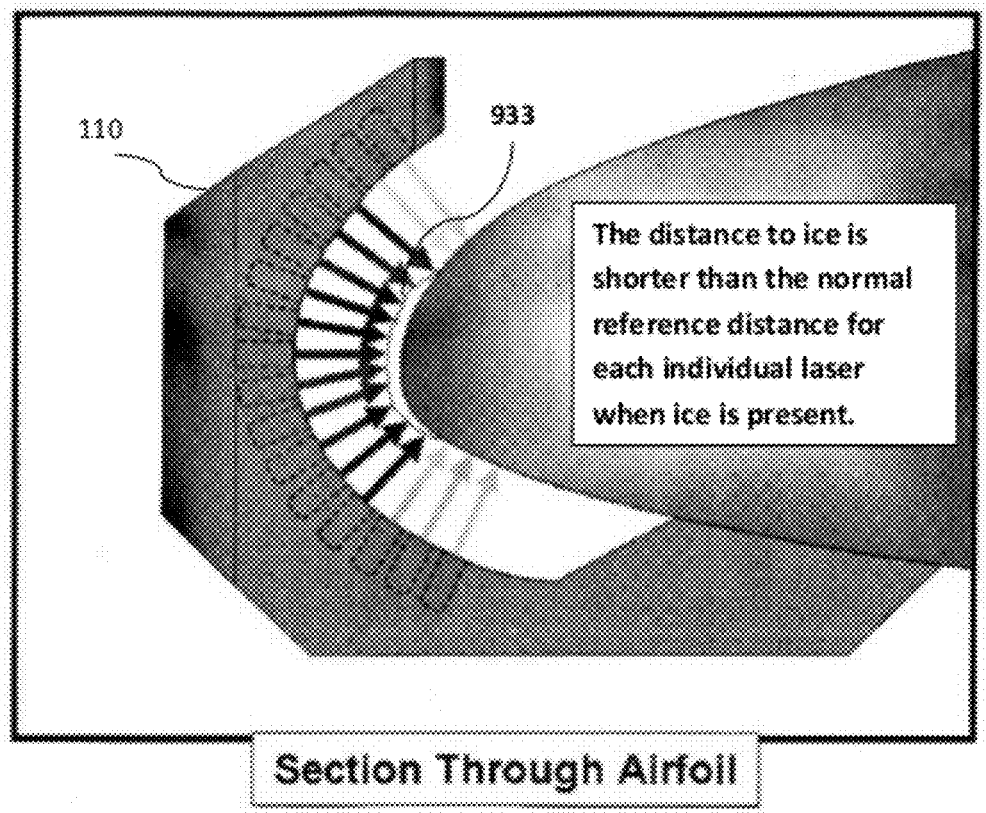
FIG. 9 shows a section view of the mounted laser probe, according to an embodiment of the present invention.

In another embodiment of the present invention as shown in FIG. 9, the laser probe 110 contains multiple laser emitters, each laser emitter individually firing laser energy (beams) on a pre-determined surface point for reflecting on a detector array. The emitters are directed to fire axially such that they fire at a point on the wing where the air is undisturbed by the probe 110 rather than firing into the surface directly facing the probe 110. Ideally the emitters will fire at a target location just to the side of the probe 110.

In the flowchart of FIG. 23b the process begins at step 2311 by firing the 1st in a series of emitters. It is assumed the laser emitters 2311 have been positioned so that each emitter is targeting a specific surface point. The measurements are recorded in step 2321. If the emitter just fired was the last in the series of emitters as determined in step 2331, then the surface contour is generated from the aggregated measurement data. If however, step 2331 determines that the current emitter that just fired is not the last emitter, then in step 2341 the next emitter in the series of emitters is fired. The process then repeats until all emitters have fired and the surface contour is generated.

It should be noted that the process steps for both FIGS. 23a and 23b are performed in the same manner for both the referential (first) measurements and the differential (subsequent) measurements. The referential measurement is the data recorded when the airplane wing is known to be "clean"—for example, after de-icing and prior to takeoff (Maybe better as using stored data derived from flight testing for the "normal" reflections in no icing conditions." These "constants" for each laser are stored in the computer and each laser pulse is compared to the "normal" constant. If a difference is detected, then it must be due to a wing contaminant. The differential measurement is the data recorded subsequent to the referential measurement. A substantial difference between the two measurements indicates a change in the surface contour of the wing such as the ice accretion 933 shown in FIG. 9.

Further, the activation of the laser probe 110, the positioning of the emitters 180, and the recording of measurement data is controlled by processor device 102 within the subsystem 112. Both the single emitter and the multiple emitter processes can be performed at pre-determined, scheduled, intervals or on an as-needed basis, such as when the pilot display 120 indicates a change in weather or atmospheric conditions. Even if the processes of FIGS. 23a and 23b are set to proceed at regular intervals, it is possible that an indication of worsening weather conditions can trigger an automatic override of the set schedule.

The number of laser emitters 180 and the pattern of the emitted laser signal (dot, line, and so forth) can be selected to meet specific user requirements. The detector array can be mounted on the fuselage or the stall fence (if available) within close proximity to the probe 110. The distance between the probe 110 and the detector array may be limited by the strength of the laser field. An average distance of one to three feet between the probe 110 and the detector array is ideal.

Receiving Sensors.

Calibrated receiving sensors 150 are mounted in another probe, or at other points on the aircraft (such as the fuselage or stall fence 635) to receive the reflected laser energy 615. Each laser emitter 180 is fired individually at target points on the aircraft. The energy fired from the laser emitter 180 hits the target point and is reflected to the laser receiving sensors 150. The receiving sensors 150 note the location of the reflected energy 615. When there is no icing, the reflected laser energy 615 falls at a known location in the receiver array; however, when icing is present, the laser reflection moves to a different spot. The locations of the reflected laser spots are correlated to define the depth and shape of the ice.

Since the temperature will vary significantly during flight and may deform the wing shape slightly, we can adjust the referential geometry measurement using the outside ambient temperature reading (OAT). This calibration makes sense for a very sensitive system. Otherwise, in a preferred embodiment, a threshold value of the difference between the referential and differential measurements is provided. This predictable and repeatable change in the laser reflection location with variations in temperature can vary greatly, depending upon aircraft and wing design and must be defined by flight test on each aircraft type.

Once defined on a particular aircraft type, the structural variations due to temperature changes can be mathematically modeled into the system. Variations in the reflected laser spot location will also occur in turbulence when the wing is flexing. Therefore, a well known mathematical routine called Kalman filtering is used to eliminate random variations caused by noise from passing snowflakes, ice particles, or water droplets in flight, along with cyclical changes in baseline geometry from aircraft flexing in turbulence.

Surface Target Area.

The purpose of the laser probe 110 is to define any changes to the surface contour of the wing. This is done by first designating a target area of the wing from which to draw the surface contour. This target area is preferably an area of approximately +/−4" above and below the center point of the wing leading edge within a short distance from the detectors. Near the center point of the leading edge is the aerodynamic stagnation point on the airfoil where ice typically forms first. The laser probe 110 is positioned so that the laser emitters 180, whether a single emitter or multiple emitters, can direct the laser energy to multiple points within the target area.

Once the target area is selected, the target points are selected within the target area to provide a detailed contour drawing. Preferably the target points are spaced no more than one-half inch apart. The laser emitters 180 are offset to view the wing in air that is undisturbed by the probe, so that the observed ice buildup will not be affected by the airflow around the probe 110.

Laser Detector Array.

Figure 21:
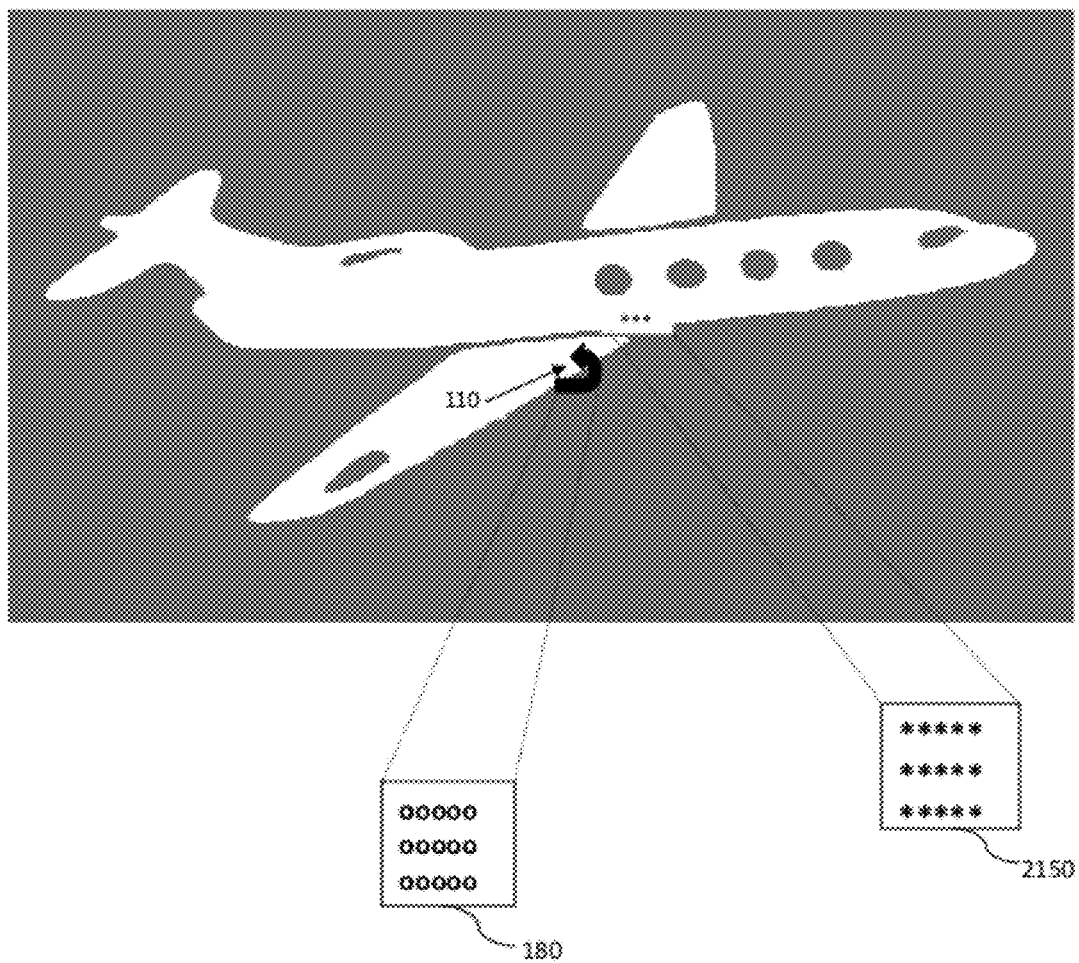
FIG. 21 shows a laser detector array according to an embodiment of the present invention.

Referring now to FIG. 21, the laser energy emitted from the laser probe 110 is reflected off the wing into a laser detector array 2150 located on the fuselage, the empennage, on a stall fence, on another part of the aircraft, or on another probe outfitted with laser detectors instead of laser emitters. The array 2150 is preferably a two-dimensional array. The numbers of rows and columns will depend on the size and spacing of the sensors. Laser detecting polymers or other similar detection and spot location devices may be used in lieu of an array of individual detectors.

As shown in FIG. 21, if using multiple emitters, the laser emitters 180 can also be arranged in an array corresponding to the detector array 2150, with a one-to-one correspondence between elements of the arrays. For example, the emitter [1,1] (row 1, column 1) will correspond to the detector [1,1]. Emitter [1,2] corresponds to detector [1,2] and so forth. One advantage of calibrating multiple emitters and sensors in this fashion is that a failure in one of the sensors in the detector array 2150 will likely indicate a failure in the corresponding laser emitter 180, which failure would otherwise be difficult to uncover.

Surface Contouring.

Figure 10A:
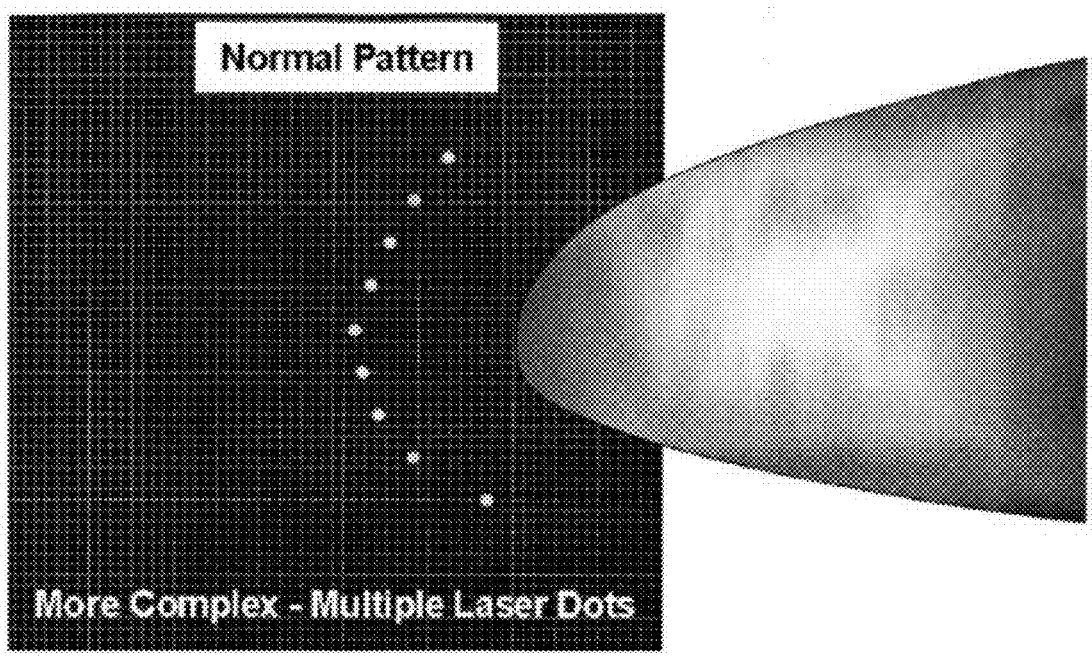
FIG. 10a through 10d show four grid views of the how the icing is detected and mapped, according to an embodiment of the present invention.
Figure 10B:
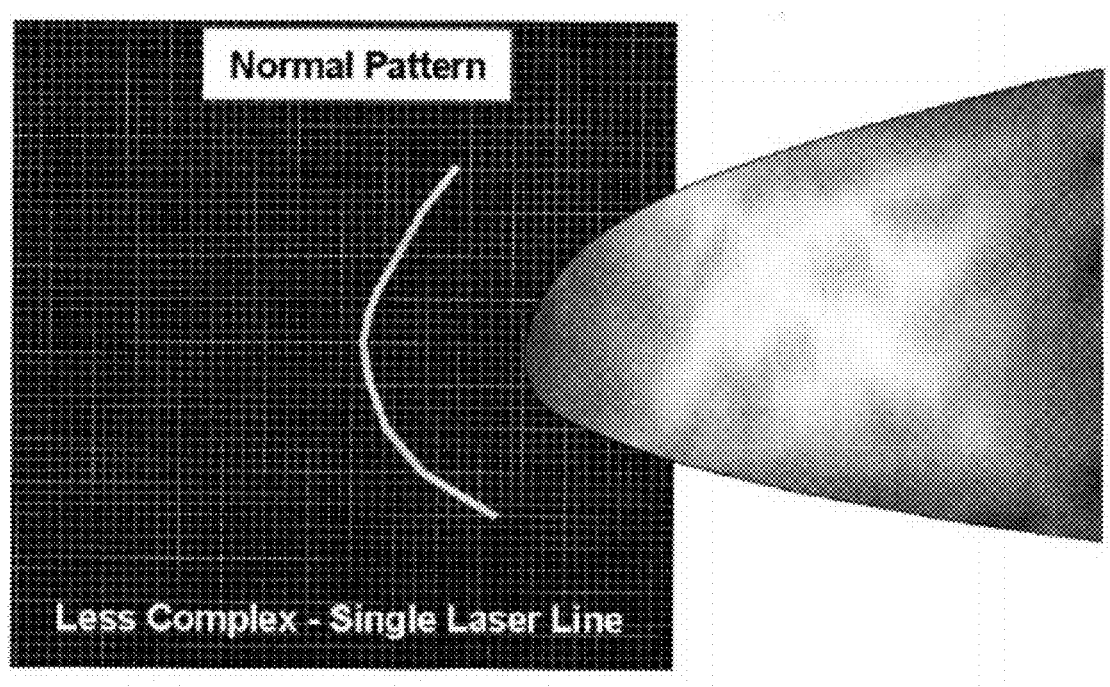

Variations in the known distance can indicate the presence and shape of ice. FIG. 10*a* shows an illustration of a normal pattern of reflected laser beams as indicated by multiple laser dots. FIG. 10*b* shows the same pattern reflected as a single laser line. The distance measurements from FIG. 10*a* or FIG. 10*b* can be used as the referential measurements.

Figure 10C:
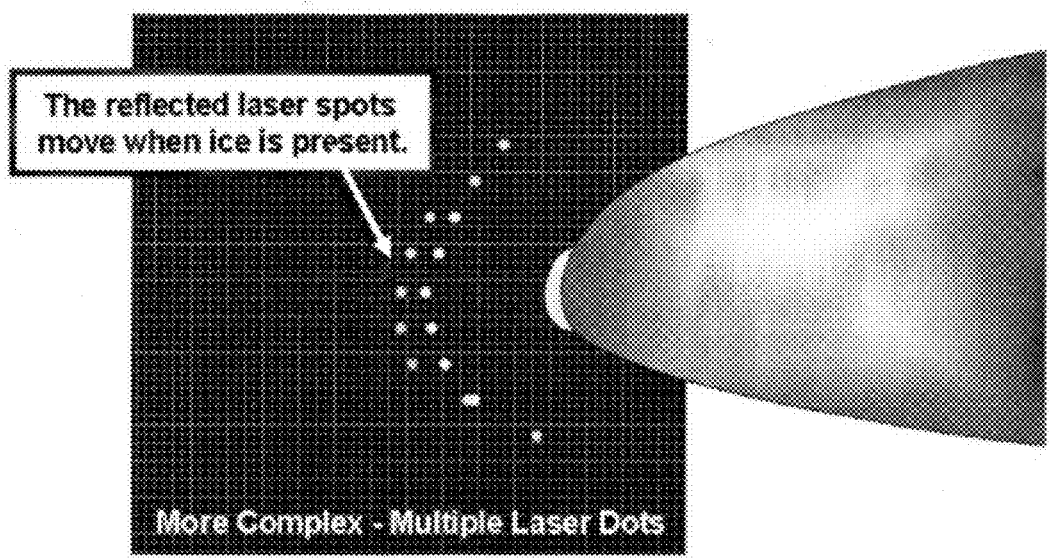
Figure 10D:
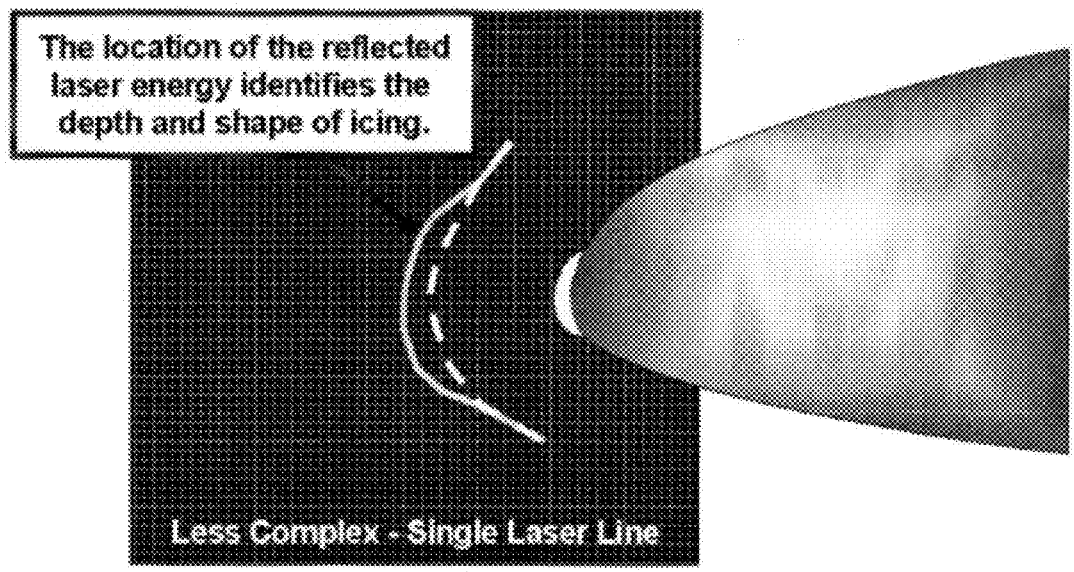

FIG. 10*c* shows how ice buildup on the wing is plotted as laser dots. The locations of the laser dots from FIG. 10*a* representing the referential (no-ice) measurement are still known. Note how not only the distance but the shape and location of the ice is also indicated by the pattern made by the laser dots. The location of the reflected laser energy identifies the depth and shape of the ice buildup. FIG. 10*d* shows the same ice buildup as shown in FIG. 10*c*, plotted as a single laser line instead of laser dots. Note that although not shown here, the differential and referential measurements can both be shown on the display, distinguished by color, shape, or other means, such as stationary/blinking blips.

The ice buildup is detected by the laser detectors when the ice first begins to form. The amount of ice buildup at each of the laser measurement points can be accurately determined because the distance to the ice buildup is shorter than the normal reference distance for each laser when ice is present. The shape of the ice buildup is approximated by displaying the differential distances as compared to the referential distance measurement for each of the target points.

Referring to FIG. 9 we see how the location, shape and depth of the ice can be determined. Because the laser probe 110 is positioned to emit laser energy at a designated target area on the airfoil, it is likely that the laser energy directed at different points will reflect different distances because the shape and location of the ice buildup differs along the points targeted by the laser emitters 180. The distances from the laser emitters to the airfoil will differ at those points where the ice buildup is found. This is how a plot of the distance measurements shows the shape, depth and the location of the ice buildup.

Multiple Laser Embodiment.

Figure 22:
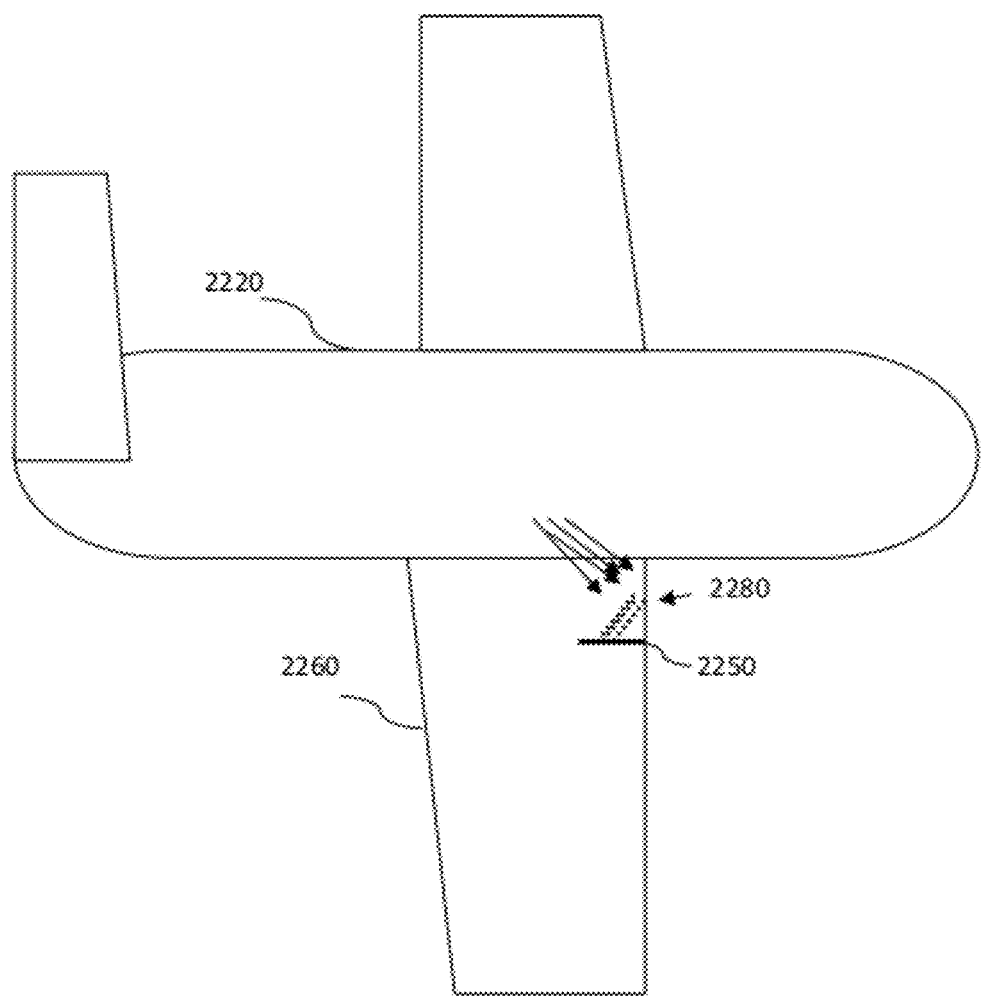
FIG. 22 shows multiple laser probes according to an embodiment of the present invention.

In an alternate embodiment as depicted in FIG. 22 the probe can be eliminated and a plurality of lasers 2210 can be mounted directly on the fuselage 2220. The multiple lasers shine from fuselage to wing 2260 and are reflected 2280 on a stall fence 2250 equipped with detectors. The number of lasers would vary according to wing size and spacing.

Dual Probe Embodiment.

Figure 8B:
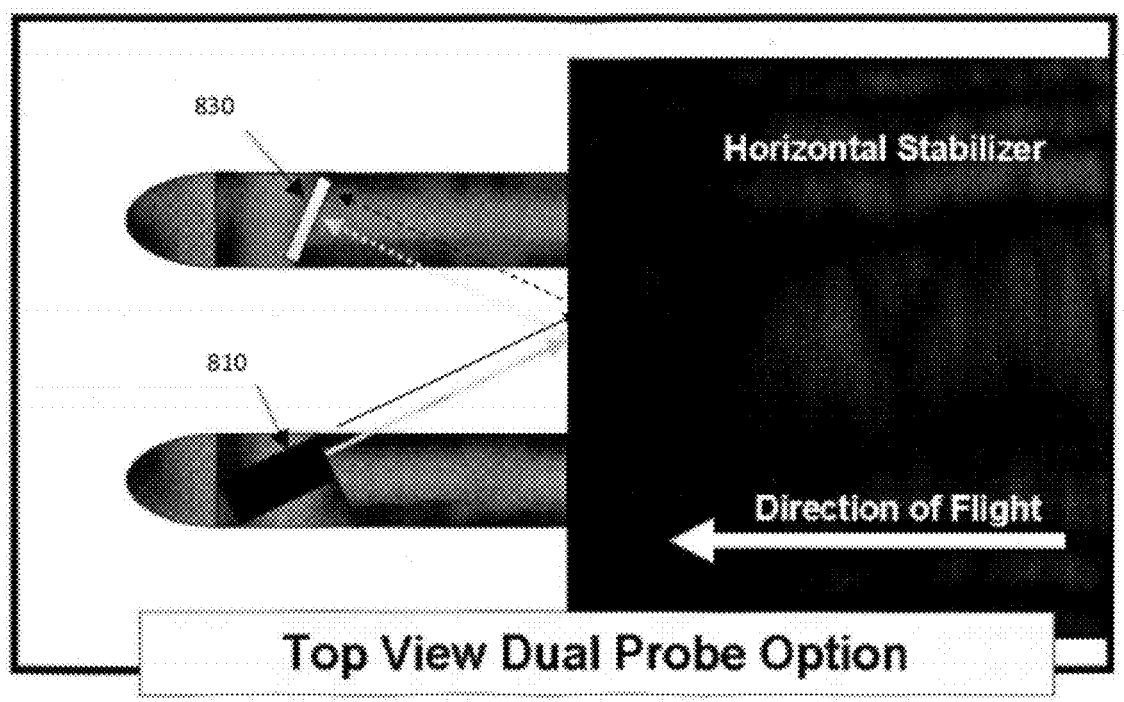
FIG. 8b shows a top view of the dual laser probe option, according to an embodiment of the present invention.

In another embodiment, dual laser probes are used, as shown in FIG. 8*b*. One probe is an emitter probe 810 and one is a receiver probe 830 with a laser receiver array when the fuselage or stall fence 635 is not feasible. This option is desirable for measurement of ice depth at the wing stagnation point but not for accurate mapping of the total icing buildup because the reflected energy will often not be on the receiver probe 830.

The Ice Detection Method.

Figure 11:
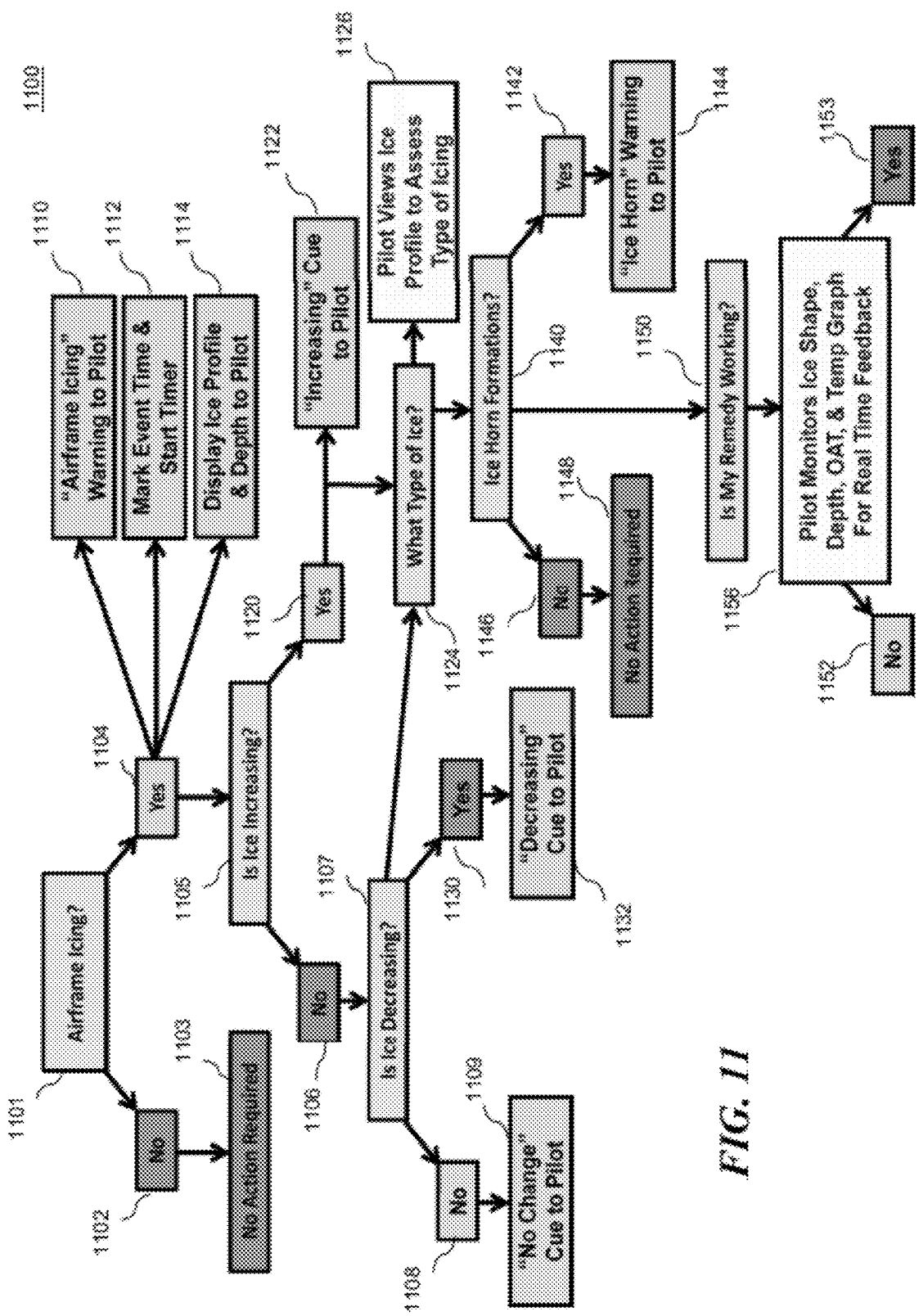
FIG. 11 shows a decision/response tree according to an embodiment of the present invention.

Referring to FIG. 11 there is shown a decision/response tree (flowchart) 1100 of an ice detection method according to an embodiment of the present invention. This flowchart 1100 is a high-level flowchart which applies to any of the previously-described embodiments. The process begins at decision point 1101 wherein it is determined whether an airframe surface contamination has been detected by the laser probe 110. If no contamination has been detected, or the contamination does not meet a pre-determined threshold value at step 1102, then no action is required (1103). Airframe surface contamination detection is determined by the difference between the referential measurements defined as "normal" when no contamination is present, and the referential measurement that is calculated by the readings from the laser probe 110.

Figure 12:
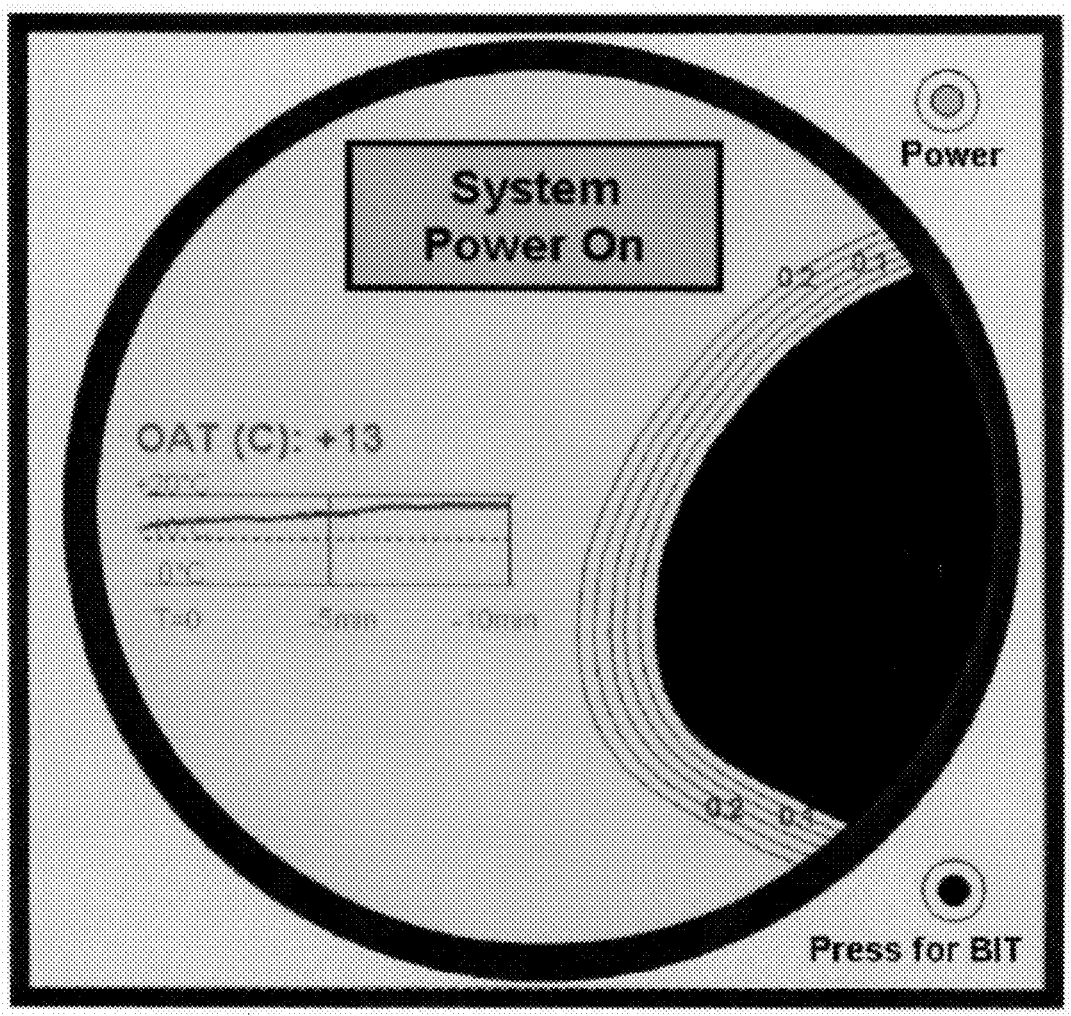
FIG. 12 shows the pilot display under conditions of no icing, according to an embodiment of the present invention.

If the difference is zero or substantially zero, then this is an indication that no contamination is present on the wing 130. Under conditions of no contamination, the pilot display 120 will be as shown in FIG. 12. If, however, the difference is greater than zero, that difference must be compared to a pre-determined value. If it is less than the pre-determined value, then this is an indication that the icing or other contamination is negligible and requires no action. If, however, the difference meets or exceeds the pre-determined value, this indicates that the contamination is substantial enough to warrant an icing event alert.

If sufficient icing has been detected at step 1104, three events will be triggered. At event 1110 an "Airframe Icing" warning is issued to the pilot. If the aircraft is so equipped, it will concurrently issue a notification to the FAA Next Generation Air Transportation System (Nextgen) or other similar system via data downlink. Preferably this warning is issued on the pilot display 1300 shown in FIG. 13. Concurrent with event 1110, event 1112 will mark the event time and start a timer 160. This is important because the rate of ice accretion can be just as important as the ice accretion itself, if not more so. Additionally, event 1114 will display the ice profile and the ice depth to the pilot on the pilot display 120. The ice profile indicates the contour, or surface shape of the ice. See FIG. 13.

At decision step 1105 it is determined whether or not the ice that was detected at step 1104 shows an increase from a prior reading. This indication of ice accretion is indicated by a variation in the measurement reading produced by the laser in both the total distance from the emitter to the detector, and the corresponding new location of the reflected laser spot (or line) on the detector array. As ice builds up on the wing of the airplane, thereby building up the "surface" against which the readings are taken, the measurement between the built-up surface and the laser is decreased.

If it is determined that the ice is increasing at step 1120, then an "Ice Increasing" cue is sent to the pilot at step 1122. At this point the type of ice detected can be determined at step 1124. Next, the pilot views the ice profile to assess the ice type at step 1126. The ice profile is a display of the surface contour as generated by the laser probe measurements. This provides an indication of the shape of the ice. Because ice horns are so dangerous, a check is made to determine whether or not the type of ice includes ice horns at step 1140. This check may include a comparison between the shape of the ice as indicated by the laser to known shapes of ice horns that are stored in memory. If the answer is no at step 1146, then no action is required at 1148.

If, however, ice horn formations have been detected at step 1142, then an "Ice Horn Warning" is issued to the pilot at step 1144. At some point during the icing encounter, the pilot will take some corrective action to reduce or eliminate the ice. From that point onward, he will be cross-checking the icing display to determine if his corrective action is working Concurrently with the issuance of the ice horn warning at step 1150, the pilot must immediately determine if his corrective action is working, because the airplane could soon lose its ability to maintain controlled flight when ice horns are present.

The pilot will then assess the viability of his corrective actions at step 1156 by monitoring the ice shape, depth, OAT, and temperature graph for real-time feedback. If the corrective action is working at step 1153, the process loops back to step 1101. If not, at step 1152 the pilot can try another corrective action, or declare an emergency and land at the nearest suitable airport.

The Pilot Display.

The pilot display provides a continuous, real-time display of existing conditions. The terms for trace, light, moderate, and severe are pilot terms to describe accumulation rates and depths of icing and are subjective. Referring to FIG. 12 there is shown a pilot display 1200 under conditions of no icing. The display 1200 shows a status indication of "System Power On;" a continuous plot of OAT readings for the last ten minutes; and a digital display of current OAT. The green "Power" illuminates when the system power is on. The "Power" light and the system display are night vision goggle (NVG) compatible. The system can be configured to automatically turn on at OAT readings less than a selected threshold (5 degrees C.), and to remain off in warm conditions.

Figure 13:
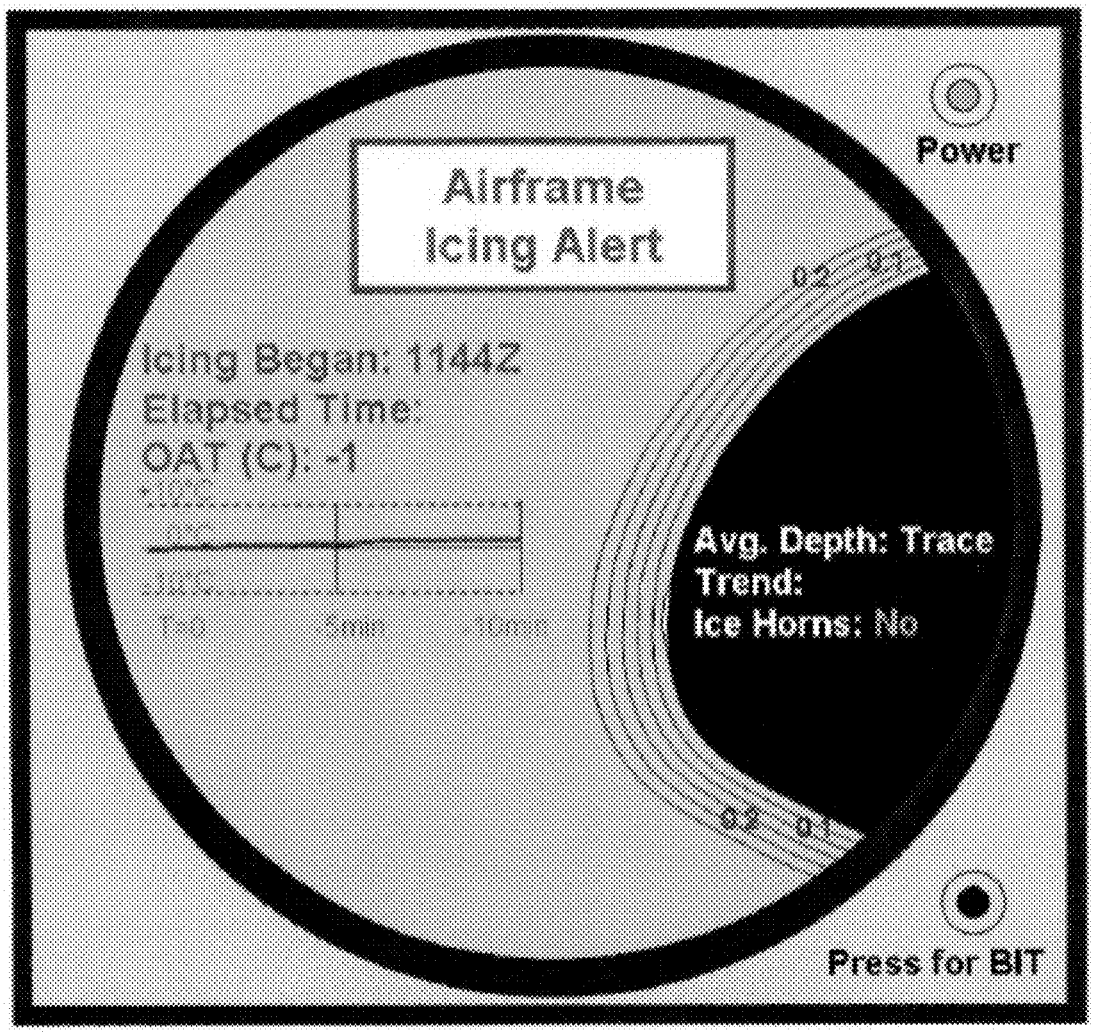
FIG. 13 shows the pilot display in Initial Icing conditions, according to an embodiment of the present invention.

Referring to FIG. 13 there is shown a pilot display 1300 in Initial Icing Conditions. The pilot display 1300 in Initial Icing Conditions mode shows: an "Airframe Icing" alert; a continuous plot of OAT readings for the last ten minutes; a digital display of current OAT; a "Time Hack" showing the time when icing was first detected; running elapsed time beginning at 1 minute intervals (or other selected small time interval); average depth is displayed as "Trace;" the trend is not displayed for the first minute, but is sampled at 10-second intervals; and an indicator showing that ice horns were not detected. This indicator for ice horns is preferably a green light, since the absence of "ice horns" is a good thing. This display 1300 effectively shows how the clock 160, timer 162 and counter 164 come into play.

Figure 14:
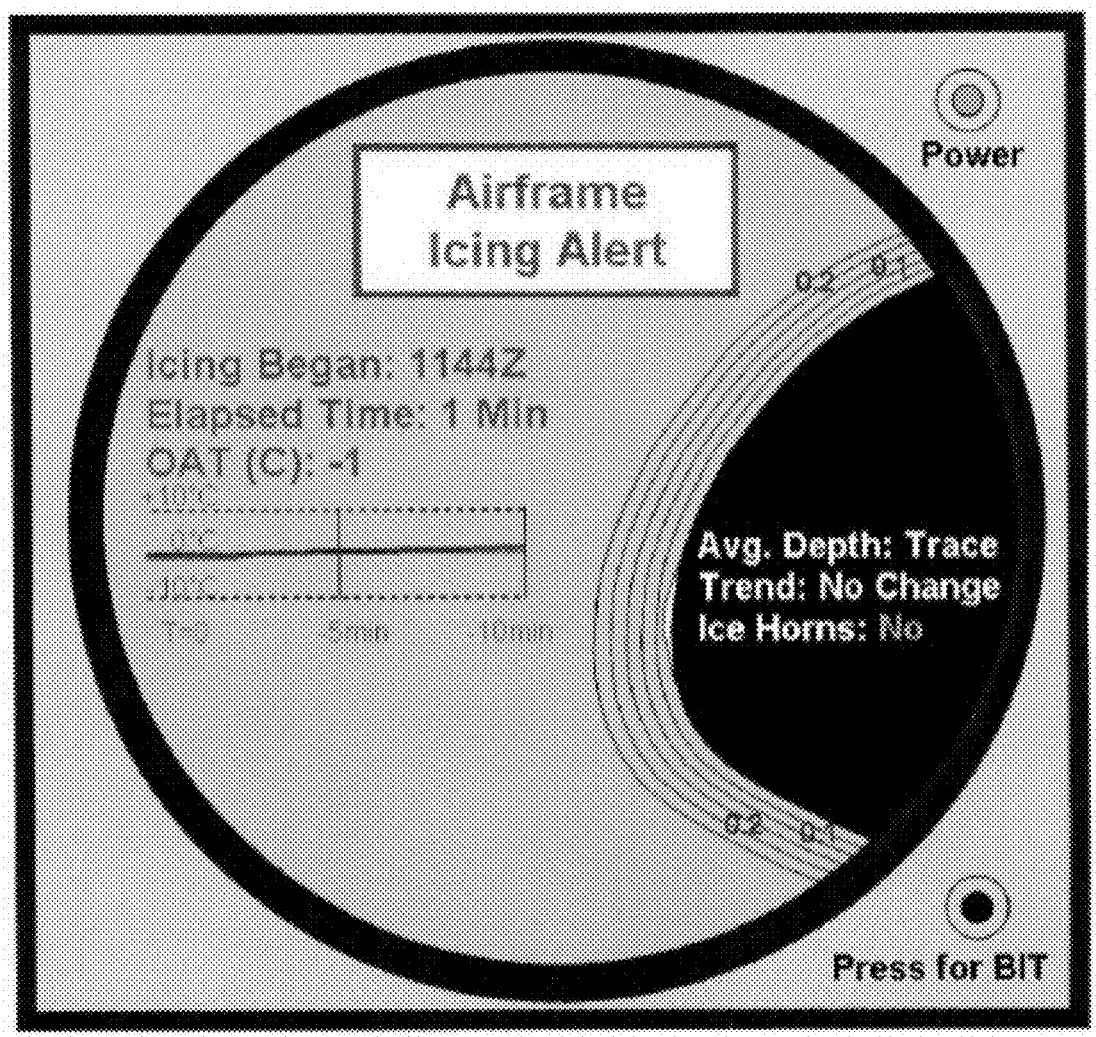
FIG. 14 shows the pilot display in Trace Icing conditions, according to an embodiment of the present invention.
Figure 15:
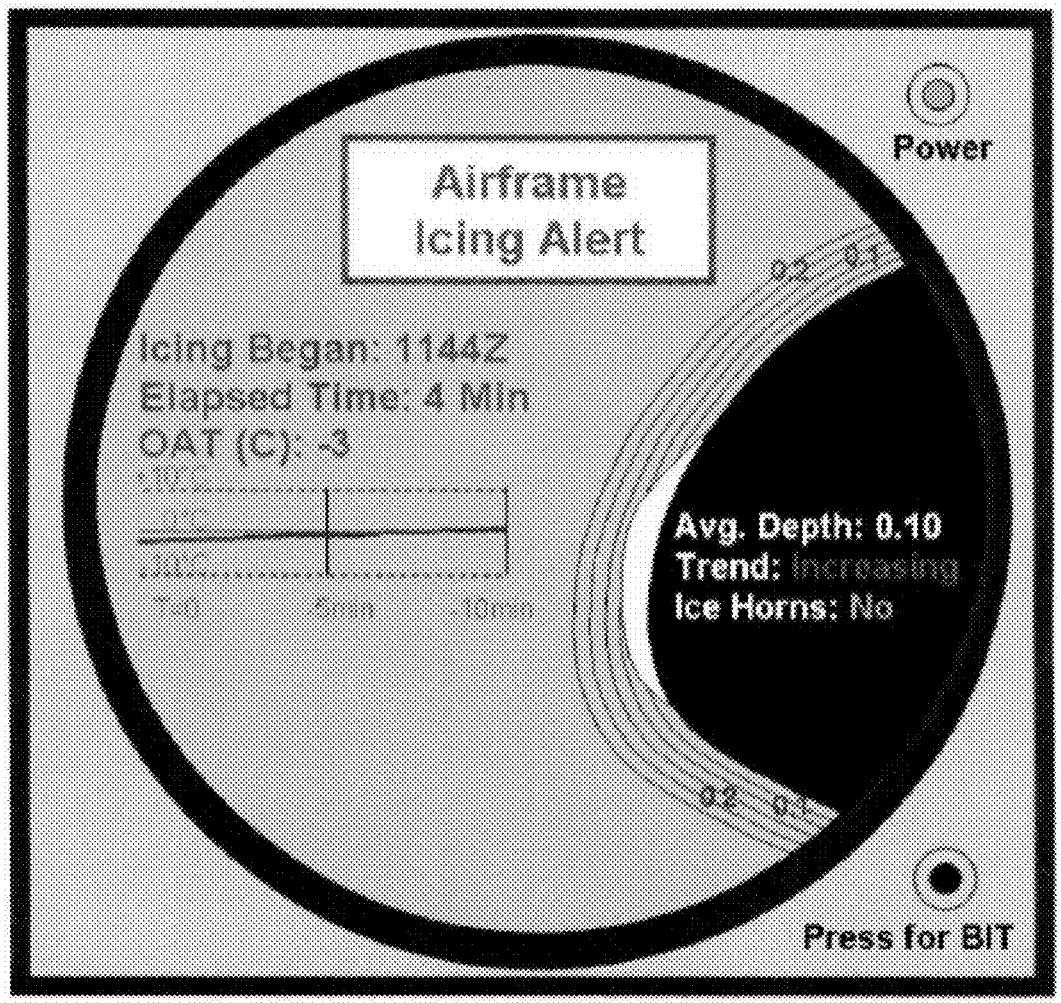
FIG. 15 shows the pilot display in Light Icing conditions, according to an embodiment of the present invention.

Referring to FIG. 14 there is shown a pilot display 1400 in Trace Icing conditions one minute after detection. The pilot's display 1400 in this situation shows: an "Airframe Icing" alert; a continuous plot of OAT readings for the last ten minutes; a digital display of a current OAT; a "Time Hack" showing the time when icing was first detected; running elapsed time now shows "1 Min;" average depth is displayed as "Trace" (Yellow); trend displays "No Change" if ice thickness and coverage is unchanged. (Yellow); and ice horns were not detected (Green). Note: The color of the average depth display can be either yellow or red, depending upon whether the depth of accumulated ice exceeds a predetermined level for that particular aircraft type. This predetermined ice depth would vary with aircraft type and which airfoil on the aircraft was being measured. It should be noted that the colors and other display features can vary within the spirit and scope of the invention FIG. 15 shows the pilot display 1500 in Light Icing Mode. The pilot's display 1500 in this mode shows: an "Airframe Icing" alert; a continuous plot of OAT readings for the last ten minutes; a digital display of current OAT; a "Time Hack" showing the time when icing was first detected; running elapsed time now shows "4 Min;" average depth is displayed as 0.10" (Pilot selectable; rounded to nearest ⅛, ¹⁄₁₆, or 2 digit decimal); trend displays "Increasing" (Red-Orange); and ice horns were not detected (Green). The OAT reading in this display shows −3 degrees C.

Figure 16:
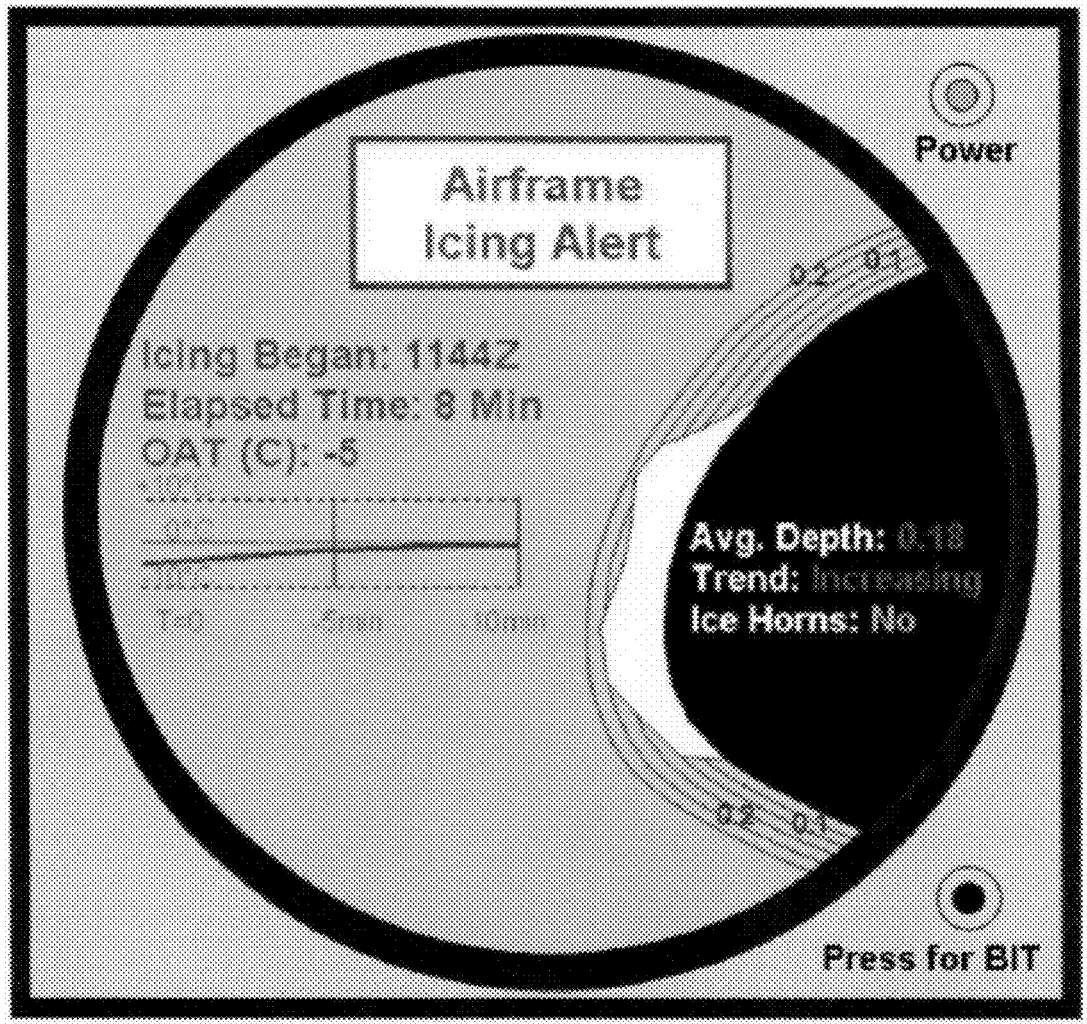
FIG. 16 shows the pilot display in Moderate Icing conditions, according to an embodiment of the present invention.

FIG. 16 shows the pilot display 1600 in Moderate Icing conditions. The pilot's display 1600 in Moderate Icing shows: an "Airframe Icing" alert; a continuous plot of OAT readings for the last ten minutes; a digital display of current OAT; a "Time Hack" showing the time when icing was first detected; running elapsed time now shows "8 Min;" average depth is displayed as 0.18 inches; trend displays "Increasing;" and ice horns were not detected (Green). The current OAT reading is reflected as −5 degree C. and the OAT plot reflects decreasing temperatures.

Figure 17:
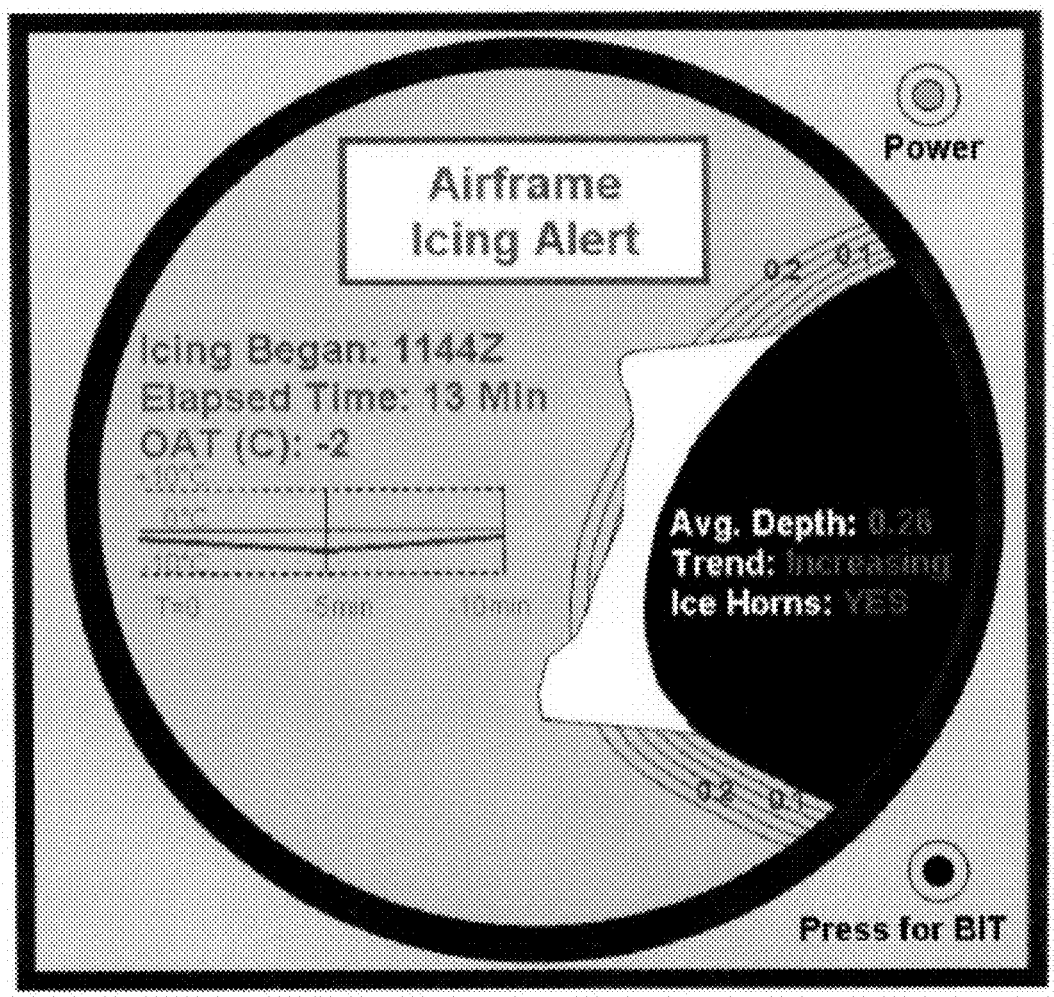
FIG. 17 shows the pilot display in Severe Icing conditions, according to an embodiment of the present invention.

FIG. 17 shows the pilot display 1700 in Severe Icing. The pilot's display 1700 in Severe Icing conditions shows: an "Airframe Icing" alert; a continuous plot of OAT readings for the last ten minutes; a digital display of current OAT; a "Time Hack" showing the time when icing was first detected; running elapsed time now shows "13 Min;" average depth is displayed as 0.26"; trend displays "Increasing;" and ice horns were detected (Red). The "Ice Horns" cue will also flash whenever ice horns are present since a stall could be imminent. In the alternative, or in conjunction with the flashing cue, an audible alarm will sound. The OAT reading is shown as −2 degrees C. and the OAT plot indicates that the temperature has been increasing for the past five minutes.

Figure 18:
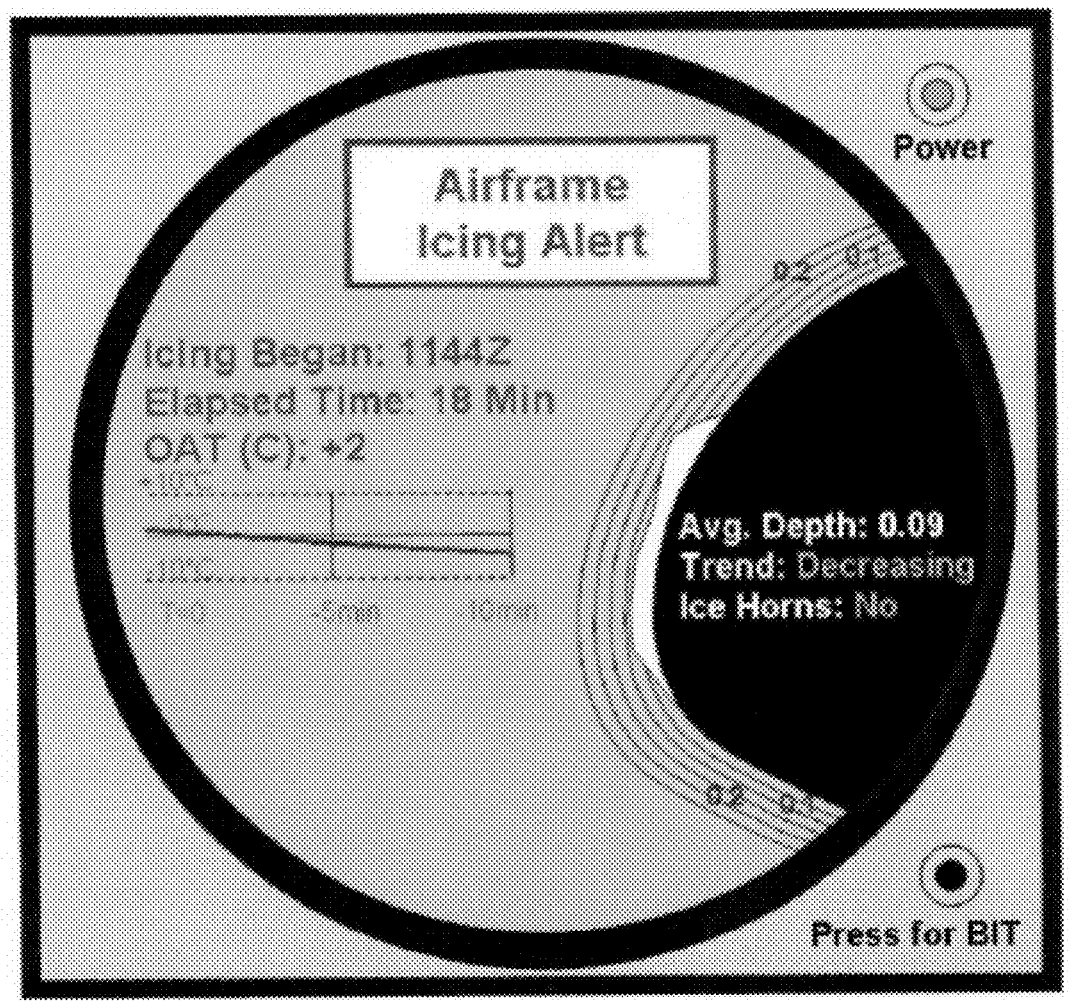
FIG. 18 shows the pilot display in Corrective Action mode, according to an embodiment of the present invention.

FIG. 18 shows the pilot display 1800 after the pilot takes corrective action eighteen minutes after detection. The pilot's display 1800 in this mode shows that the corrective action was effective because the ice is decreasing. The pilot's display now shows: an "Airframe Icing" alert; a continuous plot of OAT for the last ten minutes; a digital display of current OAT; a "Time Hack" showing the time when icing was first detected; running elapsed time now shows "18 Min;" average depth is displayed as 0.09 inches; trend displays "Decreasing" (Green); and ice horns were not detected.

Some examples of corrective action that a pilot can take responsive to the icing alert are: changing altitude to move to an altitude of warmer OAT readings (up or down); activating anti-ice mechanisms on the wing; and changing flight direction to a location with less severe icing conditions. The icing condition information for nearby locations are available to the pilot from agencies such as the FAA if the aircraft is equipped to receive digital data. If equipped, the aircraft has the potential to receive temperature, location of icing areas, and navigational information from such agencies to assist in deciding which corrective action to take. This information can be monitored and processed by the ice detection system 100 and incorporated into the display 120. For example, the location of more desirable flight areas can be presented on the display by selecting an icon visible on the display 1800.

Figure 19:
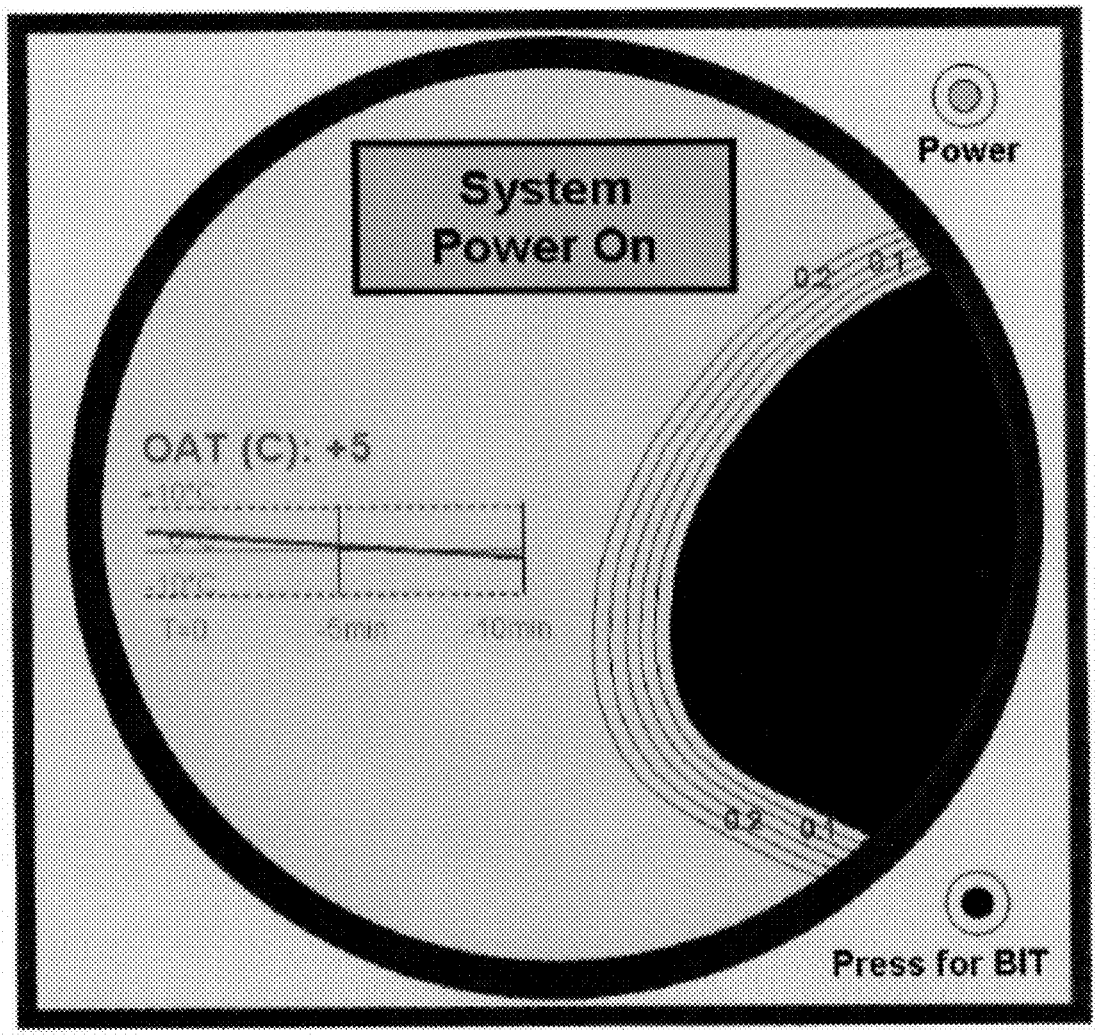
FIG. 19 shows the pilot display after corrective action is complete and there is no longer any icing according to an embodiment of the present invention.

FIG. 19 shows the pilot display 1900 after the pilot has completed his corrective action and the ice has been eliminated. The system automatically returns to its "Ready" state, ready to warn of another icing encounter. In this state, the counter 162 and timer 164 have been zeroed out. The pilot's display 1900 in Corrective Action Complete mode shows: returns to "System Power On"; maintains continuous plot of OAT readings for the last ten minutes; maintains digital display of current OAT; time hack and running elapsed time displays are removed; ice depth, trend and ice horn displays are removed.

Figure 20:
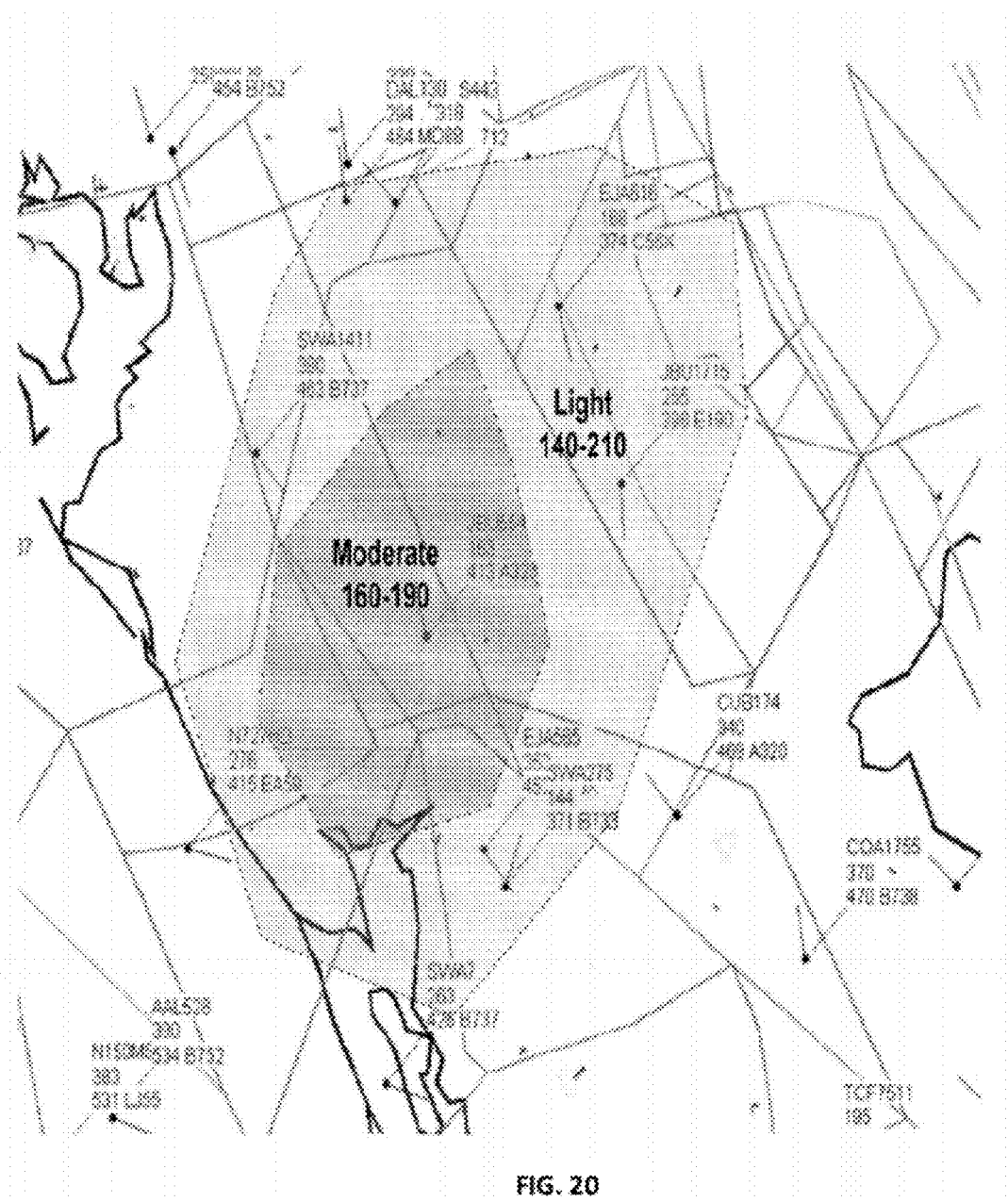
FIG. 20 shows an exemplary icing area displayed in an air transportation system, according to the known art.

Because the pilot display 1200 can track not only the amount, shape, and type of ice, but it can also track the time and location when/where the ice started and where it ended, the data shown on the pilot display 1200 can help generate a three-dimensional (3D) map of the ice boundaries. This can be done with a tie-in to the FAA or other agency data that is transmitted to the ground during flight. Once a ground system has defined the boundaries of an icing area by inputs from several aircraft, an image of the "icing area" can be on air traffic control scopes so controllers can reroute traffic to avoid the area. An image of the "icing area" can also be uplinked to aircraft to help them avoid the area. See FIG. 20 for an exemplary icing area image.

Computer Program Product.

As will be appreciated by one skilled in the art, the present invention may be embodied as a system, method or computer program product. Accordingly, the present invention will preferably take the form of a combination hardware/software embodiment, combining software and hardware aspects that may all generally be referred to herein as a "system."

Furthermore, at least one aspect of the present invention may take the form of a non-transitory computer readable program product embodied in any tangible medium of expression having computer-usable program code embodied in the medium, such as a DVD-ROM.

Therefore, while there has been described what is presently considered to be the preferred embodiment, it will understood by those skilled in the art that other modifications can be made within the spirit of the invention. The above description(s) of embodiments are not intended to be exhaustive or limiting in scope. The embodiments, as described, were chosen in order to explain the principles of the invention, show its practical application, and enable those with ordinary skill in the art to understand how to make and use the invention. It should be understood that the invention is not limited to the embodiments described above, but rather should be interpreted within the full meaning and scope of the appended claims.

I claim:

1. A method for aircraft surface contamination detection and measurement, said method comprising:
    mounting a laser probe on a first surface of an airfoil;
    positioning the laser probe to emit laser energy at a plurality of pre-determined surface points along a leading edge of the airfoil, wherein an area bounded by said surface points comprises a surface target area from which to reflect the emitted laser energy at a plurality of calibrated receiving sensors to measure a difference in the location of the reflected laser energy caused by wing contamination from icing;
    wherein the laser probe comprises at least one laser emitter for emitting the laser energy at the plurality of pre-determined surface points of the airfoil;
    using a processor device for:
        activating the laser probe to emit the laser energy to the surface target area;
        obtaining measurement data for generating a surface contour of the surface target area by:
            generating a first referential measurement of the surface target area by analyzing the reflected energy location;
            for each subsequent activation of the laser probe:
                generating a differential measurement of the surface contour of the surface target area;
                calculating a different measurement as a difference between the first referential measurement and the differential measurement;
                storing the measurement data;
                determining that a surface contamination event has been detected if the difference measurement exceeds a pre-determined amount; and
    transmitting information about the surface contamination event, said information comprising the measurement data.

2. The method of claim 1 wherein generating the differential measurement is performed continuously at timed intervals.

3. The method of claim 1 further comprising:
    using the measurement data to determine an amount, a shape, a severity, and a type of the event; and
    wherein the step of transmitting the information about the event comprises transmitting at least one of: the severity of the event; the shape of the event; the amount of the event; and the type of the event.

4. The method of claim 1 further comprising:
    using a timing device for accumulating a temporal history of the surface contamination event; and
    using a storage for storing the temporal history.

5. The method of claim 4 further comprising:
    using the stored temporal history to calculate a trend of the event; and
    transmitting an indication of the event trend.

6. The method of claim 3 wherein the step of transmitting the type of the event comprises transmitting an indication of whether or not the event is an ice horn.

7. The method of claim 6 further comprising transmitting a message to take corrective action when the indication of the severity of the event reaches a predetermined level.

8. The method of claim 1 further comprising adjusting the referential measurement if the outside ambient temperature exceeds a predetermined amount.

9. The method of claim 1 wherein mounting the calibrated receiving sensors comprises mounting the calibrated receiving sensors on a fuselage of the aircraft.

10. The method of claim 1 wherein mounting the laser probe comprises mounting the laser probe such that said laser probe extends above and beyond a leading edge of the airfoil.

11. The method of claim 1 wherein transmitting the information comprises transmitting the information for presentation on a cockpit display.

12. The method of claim 4 further comprising graphically presenting the temporal history of the event as a chart.

13. A system for aircraft icing detection and measurement, said system comprising:
  a first laser probe mounted on a first surface of an airfoil, said laser probe comprising at least one laser emitter for emitting laser energy at pre-determined surface points along an edge of the first surface, wherein an area bounded by said surface points comprises a surface target area from which to reflect the emitted laser energy at a plurality of calibrated receiving sensors to measure a difference in the location of the reflected laser energy caused by wing contamination from icing;
  the plurality of calibrated receiving sensors for receiving the energy reflected from the surface points;
  a processor device for:
    activating the laser probe to emit the laser energy to the surface target area by:
    obtaining measurement data for generating a surface contour of the surface target area by:
      generating a first referential measurement of the surface target area by analyzing the reflected energy location;
      for each subsequent activation of the first laser probe:
        generating a differential measurement of the surface contour of the surface target area;
        calculating a different measurement as a difference between the first referential measurement and the differential measurement;
        determining that a surface contamination event has been detected if the difference measurement exceeds a pre-determined amount; and
    storage for storing the measurement data and information about the icing event;
  an input/output interface for transmitting information about the icing event, said icing event information comprising the measurement data; and
  a memory operatively coupled with the processor.

14. The system of claim 13 further comprising a display for displaying the icing event information.

15. The system of claim 13 wherein the plurality of calibrated receiving sensors are located on a second probe mounted on the first surface.

16. The system of claim 13 wherein the plurality of calibrated receiving sensors are located on a second surface of the aircraft.

17. The system of claim 13 wherein the plurality of calibrated receiving sensors are disposed along a sensor array.

18. The system of claim 14 wherein the display is a cockpit display.

19. The system of claim 13 wherein the first laser probe comprises a rotating lens configured to optically redirect the laser energy.

20. The system of claim 13 wherein the first laser probe redirects the laser energy by rotating.

21. The system of claim 13 further comprising a second laser probe mounted on a second surface of the airfoil.

22. A display for presenting surface contamination event information, said display comprising:
  an operable coupling with a processor device, said processor device for:
    activating a laser probe mounted on an airfoil to emit laser energy to a surface target area;
    obtaining measurement data for generating a surface contour of the surface target area by:
      generating a first referential measurement of the surface target area by analyzing the reflected energy location;
    for each subsequent activation of the laser probe:
      generating a differential measurement of the surface contour of the surface target area by analyzing the reflected energy difference;
      calculating a difference measurement as a difference between the first referential measurement and the differential measurement; and
      determining that an icing event has been detected if the difference measurement exceeds a pre-determined amount;
  a screen for presenting the surface contamination event information, said surface contamination event information comprising the measurement data, said screen comprising a sub-display of a timing event, and a current outside ambient temperature reading;
  an operable coupling with a timing device for displaying a temporal history of surface contamination events.

23. The display of claim 22 wherein the sub-display further comprises:
  a plot of outside ambient temperature readings for a specified period of time.

24. The display of claim 22 wherein the screen further comprises an indicator of icing conditions.

25. The display of claim 22 wherein the sub-display further comprises:
  an indication that corrective action is required.

26. The display of claim 24 wherein the screen further comprises an indicator of ice horn formations.

27. The display of claim 24 where the sub-display further comprises:
  a trend of an icing event, indicating whether the icing event is increasing.

28. The display of claim 24 wherein the sub-display comprises a topographical illustration of the surface area such that a shape of the icing event can be discerned.

29. The display of claim 24 wherein the indicator of icing conditions comprises at least one of: a shape of the icing event; a depth of the icing event; a type of the icing event; and a severity of the icing event.

* * * * *